(12) United States Patent
Arigoni et al.

(10) Patent No.: US 8,071,353 B2
(45) Date of Patent: Dec. 6, 2011

(54) GENETIC REMODELING IN BIFIDOBACTERIUM

(75) Inventors: Fabrizio Arigoni, Geneva (CH); Michele Delley, Vauderens (CH)

(73) Assignee: Nestec S.A., Vevey (CH)

( * ) Notice: Subject to any disclaimer, the term of this patent is extended or adjusted under 35 U.S.C. 154(b) by 210 days.

(21) Appl. No.: 12/377,827

(22) PCT Filed: Aug. 17, 2007

(86) PCT No.: PCT/EP2007/007312
§ 371 (c)(1),
(2), (4) Date: Feb. 17, 2009

(87) PCT Pub. No.: WO2008/019886
PCT Pub. Date: Feb. 21, 2008

(65) Prior Publication Data
US 2011/0045594 A1   Feb. 24, 2011

(51) Int. Cl.
*C12N 1/00* (2006.01)
*C12N 1/22* (2006.01)
*C12N 1/36* (2006.01)
(52) U.S. Cl. .............. 435/243; 435/245; 435/252.1
(58) Field of Classification Search .............. None
See application file for complete search history.

(56) References Cited

U.S. PATENT DOCUMENTS
2008/0171073 A1* 7/2008 Stroman .............. 424/439

FOREIGN PATENT DOCUMENTS
WO  WO 0190317      11/2001
WO  WO 2006119780   11/2006

OTHER PUBLICATIONS

International Search Report for International Application No. PCT/EP2007/007312 mailed Jan. 15, 2008.
H. Tanaka et al., "Bile salt hydrolase of Bifidobacterium longum-biochemical and genetic characterization," Applied and Environmental Microbiology, Jun. 2006, vol. 66, No. 6, pp. 2502-2512.
J. Zhou et al., "Antibiotic susceptibility profiles of new probiotic *Lactobacillus* and *Bifidobacterium* strains," International Journal of Food Microbiology, vol. 98, No. 2, Feb. 1, 2005, pp. 211-217.
C. Moubareck et al., "Antimicrobial susceptibility of bifidobacteria," Journal of Antimicrobial Chemotherapy, vol. 55, No. 1, Jan. 2001, pp. 38-44.
L. Masco et al., "Antimicrobial susceptibility of *Bifidobacterium* strains from humans, animals and probiotic products," Journal of Antimicrobial Chemotherapy, Jul. 2006, vol. 58, No. 1, pp. 85-94.
K. Scott et al.,"Occurrence of the new tetracycline resistance gene tet(W) in bacteria from the human gut," Antimicrobial Agent and Chemotherapy, American Society for Microbiology, vol. 44, No. 3, Mar. 2000, pp. 775-777.
L. Meile et al., "Microorganisms as food additives: starters, protective cultures and probiotics," Mitteilungen Aus Lebensmitteluntersuchung Und Hygiene, vol. 96, No. 1, 2005, pp. 1424-1307.
J. LeDeaux et al., "Isolation and characterization of kinC, a gene that encodes a sensor kinase homologous to the sporulation sensor kinases KinA and KinB in *Bacillus subtilis*," J Bacteriol., Jan. 1995, vol. 177, No. 1, pp. 166-175.
A. Argnani et al., "A convenient and reproducible method to genetically transform bacteria of the genus *Bifidobacterium*," Microbiology, 1996, vol. 142, pp. 109-114.
F. Ferrari et al., "Construction and Properties of an Integrable Plasmid for *Bacillus subtilis*," J Bacteriol., Jun. 1983, vol. 154, No. 3, pp. 1513-1515.

* cited by examiner

Primary Examiner — Albert Navarro
(74) Attorney, Agent, or Firm — K&L Gates LLP

(57) ABSTRACT

A *Bifidobacterium* comprising a genome that is customized so as to lack an operable functional gene is disclosed. A method of making such cells is also disclosed. The method is used to make *Bifidobacterium* cells that lack certain functional antibiotic resistance genes, such as tetW, and are sensitive to antibiotics such as tetracycline.

16 Claims, 8 Drawing Sheets

GENETIC REMODELING IN BIFIDOBACTERIUM

FIELD OF THE INVENTION

This invention relates to antibiotic sensitivity in lactic acid bacteria. More particularly it relates to removal of tetracycline resistance genes in *Bifidobacterium* spp., and a method of removing or disabling genes in *Bifidobacterium* spp.

BACKGROUND OF THE INVENTION

Concern for increased bacterial resistance to available antibiotics has grown extensively in recent years. While much of the concern relates to acquired resistance attributed at least in part to the widespread use of broad spectrum antibiotics by medical practitioners, there are also some concerns about antibiotic resistance stemming from the use of bacteria for food and agricultural purposes which have acquired antibiotic resistance genes. For example, the presence and distribution of tetracycline resistance genes are common in microorganisms isolated from the environment, animals and humans including children. In some cases, antibiotic resistance may be intrinsic to a particular species—for example, due to specific cell membrane properties. Antibiotic resistance may also be acquired through mutation of bacterial genes, and it may be acquired from resistant bacteria in the environment by gene transfer.

Use of any bacterium that possesses or has acquired antibiotic resistance in food processing or agricultural production poses a potential, theoretical risk of transfer of the resistance fostering genes to other bacteria in the food, the gastrointestinal tract (GIT) of a person or animal after consumption of the food, or the environment, at some point before or after consumption. Examples of such a bacterium can be found among the *Bifidobacterium* spp., for example, *Bifidobacterium animalis* such as *Bifidobacterium animalis* subsp. *lactis* (also referred to as *Bifidobacterium animalis* subsp. *lactis* subsp. nov., previously regarded as *Bifidobacterium lactis* and sometimes referred to herein as such). One such strain, *B. animalis* subsp. *lactis* strain NCC 2818, CNCM I-3446, is commercially available, has been used for over 20 years as an additive to food products and is generally regarded as safeIt has recently been discovered that this bacterium, in common with certain other gram(−) and gram(+) bacteria of human and animal origin has a tetracycline-resistance gene, tetW, present. Although tetracycline resistance transference is theoretically possible, it has so far not been possible to demonstrate this even under laboratory conditions. It is, however, known from cloning experiments that tetW from this strain is active in gram(+) bacteria although not in gram(−) bacteria.

However, to eliminate any risk of unintended transfer of this gene, there is a need for methods for its removal from this strain. There is also a need for a variant of the strain with reduced resistance to tetracycline.

SUMMARY OF THE INVENTION

One aspect of the invention features a *Bifidobacterium* cell comprising a genome that is customized so as to lack an operable functional gene. In certain embodiments, the *Bifidobacterium* cell is a *Bifidobacterium animalis* cell, and more specifically, a *Bifidobacterium animalis* subsp. *lactis* cell. *Bifidobacterium animalis* subsp. *lactis* strain NCC 9034 is exemplified herein.

In certain embodiments, the functional gene provides antibiotic resistance; for example, the functional gene is tetW and confers resistance to tetracycline. In various embodiments, a *Bifidobacterium* cell customized to lack an operable tetW gene is at least 5-10 times more sensitive to tetracycline that a comparable cell which contains an operable tetW gene. In other embodiments, the cell is sensitive to a concentration of tetracycline greater than about 0.3 micrograms per milliter, as determined using a disk diffusion assay. An exemplary embodiment features *Bifidobacterium animalis* subsp. *lactis* strain NCC 9034, deposited as CNCM I-3664. The customized *Bifidobacterium* cell may be substantially lacking the nucleic sequence for the tetW gene. In one embodiment, the customized cell is substantially unchanged in the remainder of its genome.

Another aspect of the invention features a culture of *Bifidobacterium animalis* comprising the above-described cells.

Another aspect of the invention features a method of producing a *Bifidobacterium* cell lacking an operable predetermined functional gene. The method comprises the steps of: (1) obtaining upstream and downstream sequence for the predetermined functional gene from the *Bifidobacterium*; (2) transforming a population of the *Bifidobacterium* cells with a plasmid that is nonreplicative in the *Bifidobacterium*, the plasmid comprising the upstream and downstream flanking sequence for the functional gene and a gene encoding a selectable marker; (3) growing the *Bifidobacterium* cells under conditions allowing cells containing the gene encoding the selectable marker in the plasmid to grow, but not those cells without the gene encoding the selectable marker to grow, thereby selecting for transformants containing an integrated plasmid; (4) growing the transformants under nonselective conditions that allow growth of the cells but permit the loss of the integrated plasmid; (5) selecting cells that have lost the integrated plasmid by replica plating colonies onto plates with and without selective pressure and selecting those colonies that are sensitive to the selective pressure; and (6) confirming that the cells sensitive to the selective pressure no longer have the function of the functional gene, thereby producing a *Bifidobacterium* cell lacking an operable predetermined functional gene.

In certain embodiments, the predetermined functional gene is deleted. The functional gene can be one that confers increased resistance to an antibiotic; for example, the tetW gene confers resistance to tetracycline.

In certain of the embodiments described herein, the only functional gene that is deleted or rendered inoperable is the predetermined functional gene.

In various embodiments, the selective pressure is the presence of an antibiotic, such as spectinomycin.

In certain embodiments, the plasmid integrates into the genome by homologous recombination. The integrated plasmid may be lost through a second homologous recombination.

In various embodiments of the foregoing method, the transformants are grown under nonselective conditions for at least about 100 generations.

The above-described method may be practiced on *Bifidobacterium* cells of the species *B. animalis*, more particularly *B. animalis* subsp. *lactis*, and even more particularly *B. animalis* subsp. *lactis* strain NCC 2818. Cells that result from practice of the method on strain NCC 2818 are exemplified by *B. animalis* subsp. *lactis* strain NCC 9034.

The above-described method may also be practiced on *Bifidobacterium* cells of the species *B. longum*.

Another aspect of the invention features a *Bifidobacterium animalis* subsp. *lactis* cell that is sensitive to a concentration of tetracycline greater than about 0.3 micrograms per milliliter as determined using a disk diffusion assay. In an exemplary embodiment, the *B. animalis* subsp. *lactis* cell is strain NCC 9034.

Other features and advantages of the invention will be understood by reference to the detailed description, drawings and examples that follow.

DETAILED DESCRIPTION OF ILLUSTRATIVE EMBODIMENTS

Cells and Cultures

Figure 1:
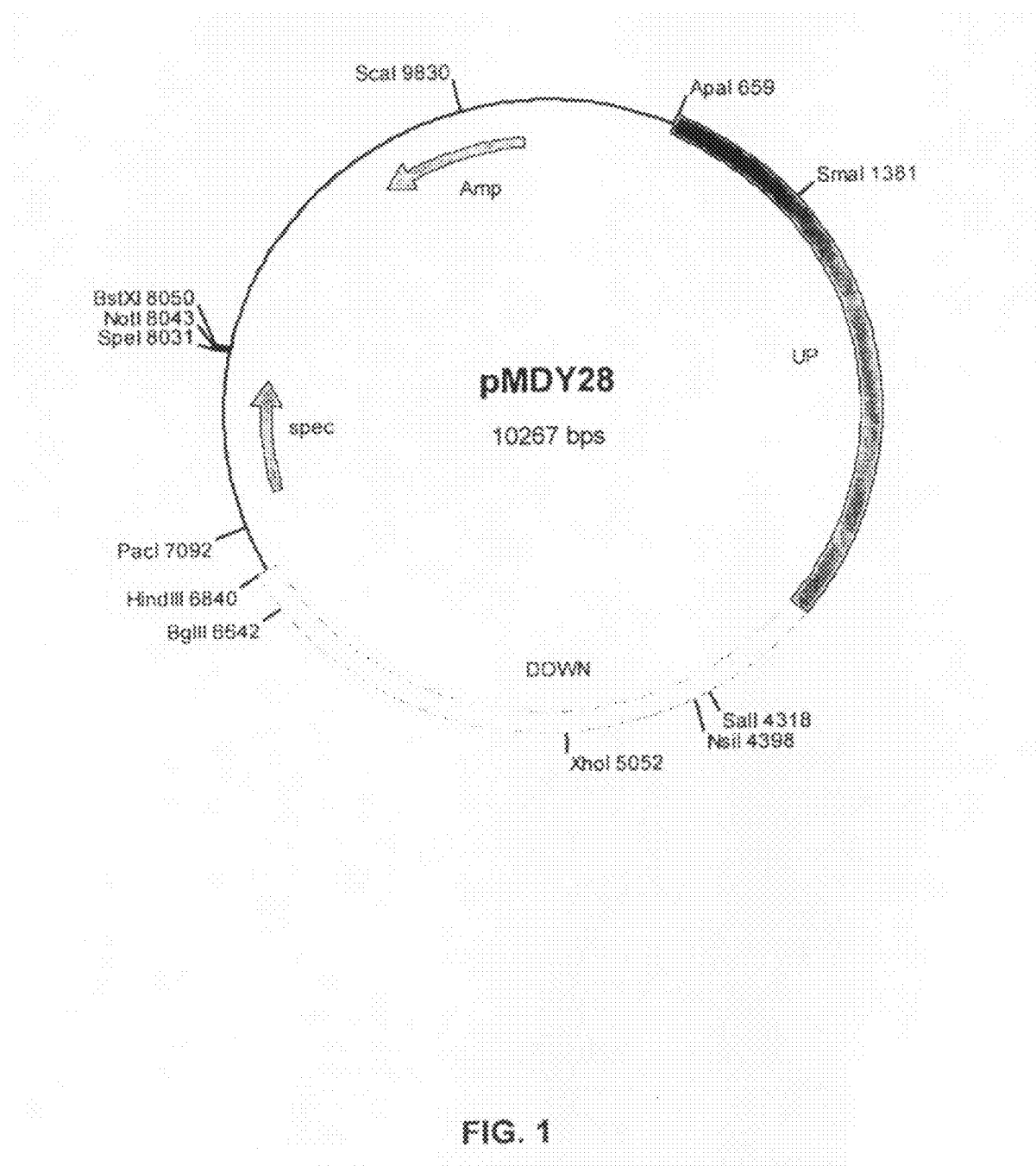
FIG. 1. A restriction endonuclease cleavage site map for pMDY28 showing the location of the spectinomycin (spec) and ampicillin (Amp) resistance markers. The tetW flanking sequences are inserted between the ApaI site (base 659) and the HindIII at 6840. The plasmid does not contain an operable on for replication in *Bifidobacterium*.

In first of its several aspects the invention provides *Bifidobacterium* cells, such as those from *B. animalis* or *B. longum*, comprising a genome that is customized so as to lack, or substantially lack, an operable predetermined functional gene. The directed disruption or deletion of any particular predetermined gene has not been accomplished in *Bifidobacterium*.

In one embodiment, the *Bifidobacterium* is a cell from a strain used in food or feed processing, or in dietary or pharmaceutical supplements. Suitable *Bifidobacterium* strains include, but are not limited to strains of *B. animalis* and *B. longum*. Also suitable are other *Bifidobacteria*, classified or not, which are intentionally added to food or feed products, or are found in food or feed products in large numbers. Other useful *Bifidobacterium* species include any cells that are directly or indirectly released into the environment as a result of manufacturing or production of food or feed, or through other commercial processes, or through the consumption of such products by humans or animals. *Bifidobacterium* species are also available in various forms intended as supplements, for either humans or animals, including human infants and baby animals, for example to treat gastrointestinal conditions such as diarrhea, or to promote healthy gut microflora. In one embodiment, the cell is a *Bifidobacterium animalis* subsp. *lactis* cell.

Although the gene to be disrupted or deleted can be any functional gene (e.g. any gene that encodes a function for the cell), in one presently preferred embodiment the functional gene provides antibiotic resistance. In particular embodiments, the gene is an acquired antibiotic resistance gene, i.e. the gene is not considered to be intrinsic to the *Bifidobacterium* cell in which it is presently found, but rather is considered extrinsic, for example derived from the environment or from another organism. In another embodiment, the functional gene codes an enzyme or enzyme inhibitor, for example an inhibitor that could negatively impact food processing or other desirable properties of the organisms (e.g., promotion of healthy guy microflora). The skilled artisan will appreciate that a variety of such inhibitors may be encoded by one or more genes. In one embodiment, the inhibitor is a protease inhibitor.

In a particular embodiment the gene product confers resistance to tetracycline. In one embodiment the functional gene is tet W. The tetW gene is known to be relatively widely-distributed. The *Bifidobacterium animalis* spp. *lactis* strain NCC 2818 is presently preferred as a source of cells containing the tetW gene to be deleted, in one embodiment. The sequence of the tetW locus is shown as SEQ ID NO.:1.

In certain embodiments, the wild-type cell is resistant to a higher concentration of the antibiotic than the cell of the invention, i.e. the cell with the deleted gene. Sensitivity of a microbial cell to a particular antibiotic may be measured in any of a variety of manners. One convenient means for measuring antibiotic sensitivity to use disk diffusion assays, for example the E-test (commercially produced by AB BIODISK). The E-test system uses a predefined gradient of antibiotic concentrations on a plastic strip and can be used to determine the exact Minimum Inhibitory Concentration (MIC) of an antibiotic for a particular organism.

In a presently preferred embodiment, a *Bifidobacterium* cell of the invention has a tetW gene disrupted, but no other functional genes are lost, and the cell is at least 5 times more sensitive to tetracycline than a comparable wild-type cell containing an operable tetW gene. In another embodiment, the *Bifidobacterium* cell with the inoperable tetW gene is at least 10 times more sensitive to tetracycline than a comparable cell which contains an operable tetW gene.

In one embodiment, the *Bifidobacterium* cell with the inoperable tetW gene is sensitive to a concentration of tetracycline greater than about 0.3 µg per milliter as determined using a disk diffusion assay.

As used herein, the term "customized" with respect to a genome indicates that the genome has been manipulated or modified by the hand of man. In certain embodiments, a genome is customized by deleting an entire locus for a particular gene. In other customized genomes, deletions of or mutations in regulatory sequences may provide complete or at least substantial loss of functionality of the predetermined gene. In addition to those genomes which have been manipulated to have a loss of an entire locus, gene, or even coding sequence, customized genomes include those with only minor alterations (including insertions or deletions), such as point mutations or frameshift mutations that result in loss, or substantial loss, of function of a functional gene.

Although it is preferred that the customization result in complete loss of operability that may not always be easily accomplished, and sometimes substantial loss of such activity will be useful. As used herein, "substantial loss indicates that more that half of the functional activity is lost, i.e. the cell with the customized genome has less than half of the functional attributes contributed by the predetermined functional gene. For example, a cell with a customized genome with respect to an enzyme will have less than 50% of the activity of that enzyme when compared to the parent cell from which it is derived. Alternatively, a cell with a customized genome can produce less than 50% of the gene product associated with the predetermined functional gene. The skilled artisan will appreciate that in dealing with certain functional activities, a cell having less than 50% of the gene product for a particular functional gene may not always have a 50% loss of measurable activity in the cell.

Preferably in a customized genome, there is at least a point mutation or a frameshift mutation in the coding sequence itself, so as to prevent transfer of an intact functional gene to other cells in proximity to, or in the environment of the cell with the customized genome. Thus, as used herein, "customized" requires that there be manipulation of the genome, where such manipulation is directed at loss or substantial loss of the operability of a predetermined functional gene.

Accordingly, in one embodiment, the functional gene is deleted altogether, or at least substantially deleted. This embodiment ensures that no functional antibiotic resistance gene can be inadvertently transferred to the environment, other gut microbes, or other organisms in the environment, and it also ensures that not even a disrupted gene can be transferred only to be restored through a downstream event. Thus, in a preferred embodiment, the *Bifidobacterium* cell according to this aspect of the invention is substantially lacking the nucleic sequence for the tetW gene. In one embodiment the coding sequence is at least substantially deleted. Alternatively, one or more noncoding sequences related to the predetermined functional gene may also be deleted. For example binding sequences or regulatory sequences for the functional gene that serve no other function in the cell, may be deleted. In other embodiments the cell with the customized genome has a more subtle alteration, for example a point mutation or a frameshift mutation that results in the loss or substantial loss of functionality of the predetermined gene, e.g. the genome that is customized has reduced operability of the functional gene.

Also in a preferred embodiment, the *Bifidobacterium* cell is substantially unchanged in the remainder of its genome. In other words, other than the loss of the operability of the functional gene, and preferably its complete or at least substantial deletion from the cell, the *Bifidobacterium* cell is identical, or nearly so, with the cell from which it is derived (e.g the parental cell). This is particularly useful where a strain or culture have been adapted for a long period of time to provide desirable properties useful for example in food processing, such as fermentation of dairy products, for example yoghurt and the like. For example, in one embodiment described in more detail below, where *B. animalis* subsp. *lactis* NCC2818 is the starting (parent) cell, and tetW is the predetermined functional gene, the resultant cell is *B. animalis* subsp. *lactis* NCC 9034, the customized genome of which differs from the parent only in lacking the predetermined tetW gene. As expected, the cells are also phenotypically comparable except for the increased sensitivity to tetracycline exhibited by the NCC 9034 cells. The foregoing embodiments are also useful for strains which are used to help treat clinical conditions, particularly where those strains have been selected or developed to have desirable functions such as rapid generation times or extended residence times in the gut.

In another of its several aspects, the invention provides a culture of *Bifidobacterium* comprising a cell with a deleted, or at least inoperable functional gene. The use of such cultures need not be discussed at length as the skilled artisan will appreciate them. In one embodiment, the culture comprises a cell derived from a known culture, the known culture discovered or determined to have in its genome an undesirable functional gene. In one embodiment, the gene is an extrinsically acquired gene, such as a gene encoding antibiotic resistance. In one embodiment the gene is a tetracycline resistance gene. In a specific embodiment the gene is a tetW gene, and in particular embodiments the pertinent tetW gene sequence is that provided in SEQ ID NO.:1.

Methods of Making the Cells and Cultures

In another of its aspects, the invention provides methods of producing a *Bifidobacterium* cell lacking an operable predetermined functional gene. The method comprising the steps of:

obtaining upstream and downstream sequence for the predetermined functional gene from the *Bifidobacterium*;

transforming a population of *Bifidobacterium* cells with a plasmid that is nonreplicative in the *Bifidobacterium* and comprises the upstream and downstream flanking sequence for the functional gene, as well as a gene encoding a selectable marker;

growing the *Bifidobacterium* cells under conditions that allow only cells containing the gene encoding the selectable marker in the plasmid to grow, thereby selecting for transformants that have integrated the plasmid into the chromosome at the locus of the functional gene;

growing the transformants under nonselective conditions that allow growth of the cells but permit the loss of the integrated plasmid;

selecting cells that have lost the integrated plasmid by replica plating colonies onto plates with and without selective pressure for the gene encoding the selectable marker and selecting those colonies that are sensitive to the selective pressure;

confirming that the cells sensitive to the selective pressure no longer have the function of the functional gene, thereby producing a *Bifidobacterium* cell lacking an operable predetermined functional gene.

As with the description of the cells and cultures above, preferably the *Bifidobacterium* cell is a cell from a strain used in food or feed processing, such as *B. animalis* or *B. longum*. Other *Bidifidobacteria* are contemplated for use herein, such as those used in clinical treatment of humans or animal, or used preventatively therein. In one embodiment the cell to be used as the starting cell is a *Bifidobacterium animalis* subsp. *lactis*. In certain embodiments exemplified herein, the *B. animalis* subsp. *lactis* cell is strain NCC 2818 (commercially available as "BB12" from Chr. Hansen).

In a one embodiment the gene to be rendered inoperable or deleted encodes resistance to tetracycline. In one embodiment the functional gene is tetW. In one embodiment the tetW gene has the sequence provided as SEQ ID NO.:1, which represents the entire tetW locus in *B. animalis* subsp. lactis NCC 2818. In one embodiment, the starting cell is *Bifidobacterium animalis* subsp. *lactis* cell strain NCC 2818. Samples of these cells have been deposited in the patent repository of the Pasteur Institute, 25, rue du Docteur Roux, F-75724 Paris Cedex 15 (France), on Aug. 22, 2006 under the terms of the Budapest Treaty as deposit number CNCM I-3446. When *B. animalis* subsp. lactis NCC2818 is the starting cell, and tetW is the predetermined functional gene, the resultant cell is *B. animalis* subsp. lactis NCC 9034, samples of which have also been deposited in the patent repository of the Pasteur Institute, 25, rue du Docteur Roux, F-75724 Paris Cedex 15 (France), on Aug. 22, 2006 under the terms of the Budapest Treaty as deposit number CNCM I-3664.

In certain embodiments, the wild-type cell is resistant to a higher concentration of the antibiotic than the cell that results from the methods provided. Disk diffusion assays and related sensitivity tests such as the E-test (AB BIODISK) are preferred ways of measuring the sensitivity of a cell to an antibiotic. The Minimum Inhibitory Concentration (MIC), however determined, of an antibiotic for a particular organism is a convenient way to compare relative sensitivities.

In a presently preferred embodiment, a *Bifidobacterium* cell of the invention has a tetW gene disrupted or deleted, but no other functional genes are lost or disrupted in terms of their function. In one embodiment, the cell produced by the methods is at least 5 times more sensitive to tetracycline than a comparable wild-type cell containing an operable tetW gene. More specifically, the resultant *Bifidobacterium* cell is at least 10 times more sensitive to tetracycline than a comparable cell which contains an operable tetW gene. In other embodiments the cell is 20, 30, 40 or even 50 or more times as sensitive than a comparable cell that retains the tetW gene. In a particular embodiment, the resultant *Bifidobacterium* cell is sensitive to a concentration of tetracycline greater than about 0.3 µg per milliter, as determined using a disk diffusion assay or the E-TEST.

As above for the cells and cultures, in one embodiment, the functional gene is deleted altogether, or at least substantially deleted, such that no functional antibiotic resistance gene can be inadvertently transferred to the environment, other gut microbe, or other organisms in the environment. Similarly, not even a disrupted gene can be transferred as substantially all of the sequence has been lost from the organism. Thus, in such an embodiment, the resultant *Bifidobacterium* cell made in accordance with the methods is substantially lacking the nucleic acid sequence for the tetW gene. In various embodiments the coding sequence is at least substantially deleted, and even noncoding sequences related to the predetermined functional gene are also be deleted.

In a presently preferred embodiment, the resultant *Bifidobacterium* cell genome is substantially unchanged except for the gene deleted or rendered inoperable. Preferably the genome of the resultant *Bifidobacterium* cell is identical, or nearly so, with the cell from which it is derived (e.g. a parent cell), other than the functional gene rendered inoperable or deleted. Thus, the cells produced by the method will have substantially, or even exactly the same functionality and properties (such as nutritional requirements, enzymatic profiles, growth characteristics, flavor production, and acid production) as the parent, wild-type, or archetype strain from which they are derived. Thus, the cells so produced can be used to generate useful cultures of *Bifidobacterium* comprising a cell with a deleted, or at least inoperable functional gene. This is especially true where cell is derived from a known culture, where the known culture is discovered to have in its genome an undesirable functional gene, such as an acquired antibiotic resistance gene, for example, a tetracycline resistance gene, particularly a tetW gene.

In one embodiment of the method, the plasmid encodes an additional selectable marker. In certain embodiments the selectable marker confers antibiotic resistance. In such embodiments, the selective conditions for screening transformants for the integrated plasmid include selective pressure in the form of the antibiotic corresponding to the resistance marker. In one embodiment, the antibiotic is spectinomycin, in another it is chloramphenicol.

In certain embodiments, the plasmid integrates into the genome by homologous recombination, preferably at the site of the upstream and/or downstream flanking sequences; a crossover event occurs that allows the circular plasmid to become integrated into the *Bifidobacterium* genome. In another embodiment, the integrated plasmid is lost through a second homologous recombination event, preferably with the concomitant loss of all or substantially all of the predetermined functional gene—e.g. the tetW locus or other gene targeted.

As stated above, in a preferred embodiment, the only functional gene that is deleted or rendered inoperable is the predetermined functional gene.

In one embodiment, the transformants are grown under nonselective conditions for a sufficient number of generations to allow the loss of the unneeded sequences, including the predetermined functional gene. In one embodiment, growth for at least about 100 generations will promote such a loss.

The following examples are provided to further illustrate these or additional aspects of the invention, and should not be construed to limit the invention to what is exemplified.

EXAMPLES

Construction of a Non-Replicative Plasmid

DNA fragments of approximately 3 kb flanking Let W upstream of its start codon and downstream of its stop codon were amplified with the following primer pairs:

```
mdy100:    5'-CGCACCGGGCCCCCTCACGCAAACTCTACG-3';              (SEQ ID NO.: 2)

mdy98:     5'-TGTGGTGTATCACATGTGATTGTCCTCCCTTTA-3'            (SEQ ID NO.: 3)
and mdy99:     5'-AGGACAATCACATGTGATACACCACAGCGAGG-3'             (SEQ ID NO.: 4)

mdy89:     5'-CCGTCCAAGCTTTCTATCGCGAGATAATCAGC-3').           (SEQ ID NO.: 5)
```

The resulting amplified products were used as template to perform a fusion PCR with primers mdy00 and mdy89, which resulted in a DNA fragment that contained the upstream and downstream region of tetW joined together via the start and stop codon of tetW.

The DNA fragment was digested at its extremities by HindIII and ApaI and cloned into pJL74 (Ledeaux and Grossman, *J. Bacteriol.* 1995 January; 177(1):166-75.) between HindIII and ApaI. The resultant plasmid was named pMDY28 (SEQ ID NO.:6). A detailed restriction endonuclease site map is provided as FIG. 1. The sequence of the DNA fragment inserted into pJL74 to form pMDY28 was verified and shown to be identical to that from the chromosome of *B. animalis* subsp. *lactis* NCC 2818. This indicated that no mutations were introduced during the PCR-mediated DNA amplification, nor during the subsequent manipulations of the DNA.

Transformation of *B. animalis* and Allelic Exchange

Plasmid pMDY28 was transformed into *B. animalis* cells using the method described by Argnani et al. 1996 (*Microbiology;* 142:109-14.). Cells were placed onto MRS plates containing 100 mg spectinomycin per liter. The resulting spec$^R$ transformants were selected anaerobically. Since the plasmid pMDY28 cannot replicate in *B. animalis*, spec$^R$ colonies most likely resulted from the plasmid being integrated into the *B. animalis* genome by homologous recombination via a single cross-over event. Successful transformation of a nonreplicative plasmid into *Bifidobacterium* cells has not been previously reported.

The spec$^R$ transformants were cultivated for approximately 100 generations in MRS broth without antibiotic selection to allow loss of the plasmid and individual colonies were plated on MRS agar medium. In order to ensure that the plasmid was removed from the genome of *B. animalis*, individual colonies were tested for loss of spectinomycin resistance by replica plating on MRS agar with and without spectinomycin added.

Out of 750 colonies tested, 163 colonies were spectinomycin sensitive (21%) indicating that the plasmid had been excised from the chromosome of *B. animalis* through the occurrence of a second cross over event.

A second such event could result in two genomic configurations:
 i) reversion to the wild type configuration with a tetW locus identical to wild type cells, or
 ii) deletion of tetW.

In order to distinguish between these two possibilities, 135 out of the 163 spectinomycin sensitive colonies described above were tested for the loss of tetW by direct colony PCR with the following primer pair:

```
mdy94:    5'-GAGCATGTATTCGGTGTCG-3'      (SEQ ID NO.: 7)
and mdy95:    5'-GATTTGCCCTATCGACTG-3'.      (SEQ ID NO.: 8)
```

Figure 2:
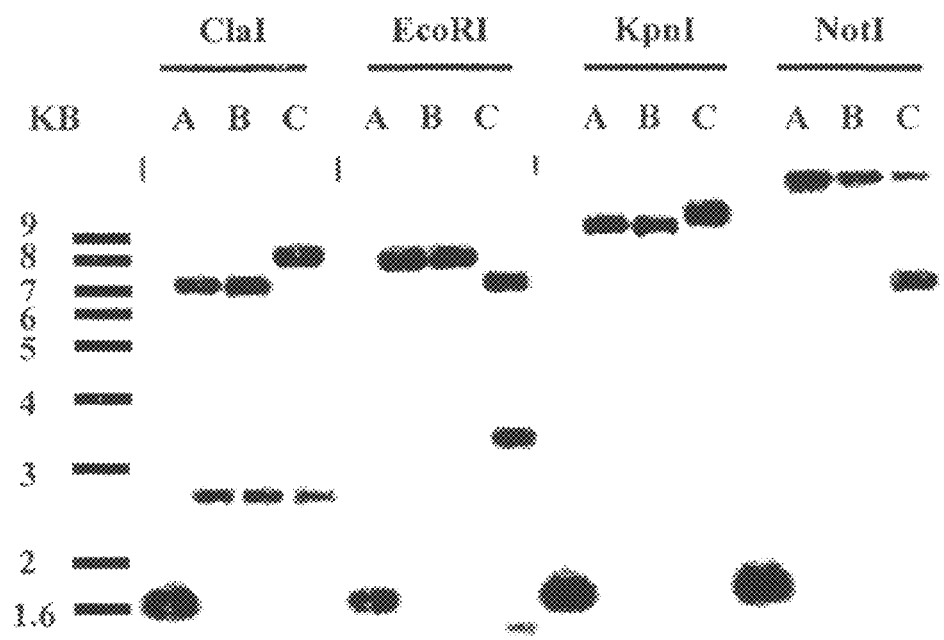
FIG. 2. Top panel shows the Southern blot analysis for ClaI, EcoRI, KpnI and NotI restriction fragments of genomic DNA obtained from two independent mutants (lanes designated A, and B). Lane C contains comparable fragments obtained from the wild-type strain (NCC 2818) used to create the mutants. Bottom panel shows the sizes of the fragments observed on the Southern blot obtained for the mutants (A&B) versus those obtained for the wild-type strain.

Of the 135 colonies tested, two gave raise to a DNA band of 1034 bp indicating a deletion of tetW whereas the others resulted in a PCR fragments of higher molecular weight (2949) similar to that obtained with wild-type cells (See FIG. 2, Panel B).

Southern Blot Analysis of tetW Deletion Mutants

Deletion of tetW was confirmed by PCR and Southern blot analysis with genomic DNA extracted from the two candidate mutants identified by PCR analysis (see FIG. 2, Panels A & B)). Chromosomal DNA samples were digested with restriction enzymes (ClaI, EcoRI, or NotI). Southern blots were hybridized with DNA from pMDY28. Southern analysis confirmed that tetW had been deleted from the genome of both candidates mutants (Lanes A&B). Only one strain was retained; it was subsequently designated NCC 9034.

Antibiotic Sensitivity Testing of *B. animalis* Subsp. *lactis* Strain NCC 9034 Versus NCC 2818

The tetracycline sensitivity of the *B. animalis* subsp. *lactis* wild-type strain NCC 2818 was compared with that of the derived strain NCC 9034 which was shown to have substantially all of the tetW gene deleted. A commercial E-TEST (AB BIODISK) was used to determine the MIC for tetracycline of each strain.

Figure 3:
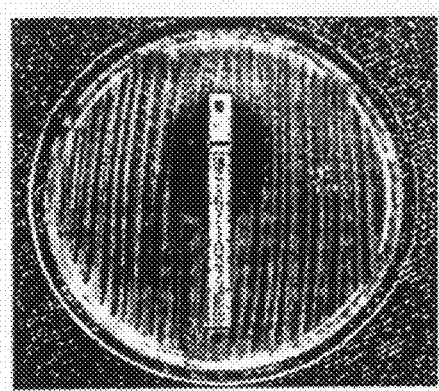
FIG. 3. Resistance of *Bifidobacterium animalis* subsp. *lactis* strains NCC 362 (wild-type) (left panel, approximately 16 μg/ml tetracycline) and NCC 9034 (right panel, approximately 0.3 μg/ml tetracycline) to the antibiotic tetracycline as determined with an E-TEST to determine minimum inhibitory concentration (MIC).
Figure 3:
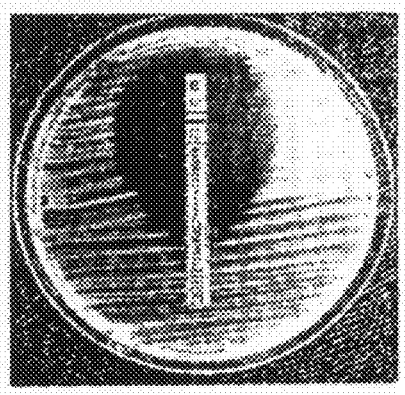
Figure 4:
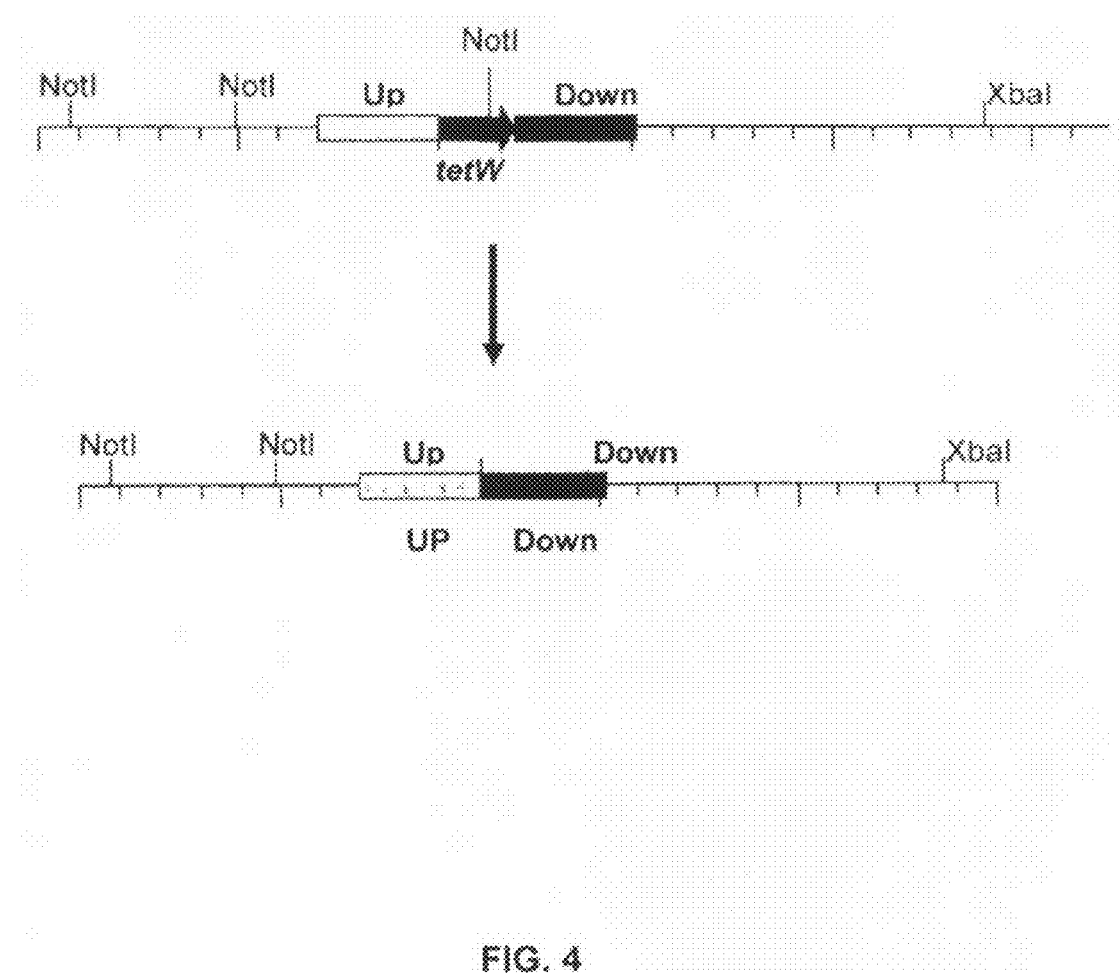
FIG. 4. Map of the tet loci for NCC 362 (top panel) and the NCC 9034 (bottom panel) strains, showing the absence of the tetW gene in the latter strain. The tetW flanking sequences used to create the knock-out mutant are shown in the shaded bars in both panels.

The results are shown in FIG. 3. While strain NCC 2818 had a MIC of 16 μg/ml, NCC 9034 was more susceptible to tetracycline, having an MIC of only about 0.3 μg/ml. thus, NCC 9034 was about 50 times more sensitive to tetracycline than its parent wild-type strain NCC 2818. This sensitive phenotype is completely consistent with the loss of the functionality of the tetW gene. As seen in the Southern analysis above, this is supported by the gene analysis.

Deletion of a *B. longum* Gene (Bl0108) Encoding a Protease Inhibitor Protein.

Construction of a Non-Replicative Plasmid

DNA fragments of approximately 3 kb flanking Bl0108 were amplified with the following primer pairs:

```
mdy82:    5'-CGACCCAAGCTTGGATCGGCTCGTGCATCATTGC-3';    (SEQ ID NO.: 9)

mdy83:    5'-GCAAACCGTACCTCAATACC-3'                    (SEQ ID NO.: 10)
and mdy84:    5'-CGACCCAAGCTTGCAGTCCGTCAATTAGGGTG-3'        (SEQ ID NO.: 11)

mdy85:    5'-CGTTGCTGACGTTGCGGTTC-3').                  (SEQ ID NO.: 12)
```

The PCR products obtained with mdy82 and mdy83 were digested with EcorI and HindIII. The PCR products obtained with mdy84 and mdy85 were digested by HindIII and SalI.

Figure 5:
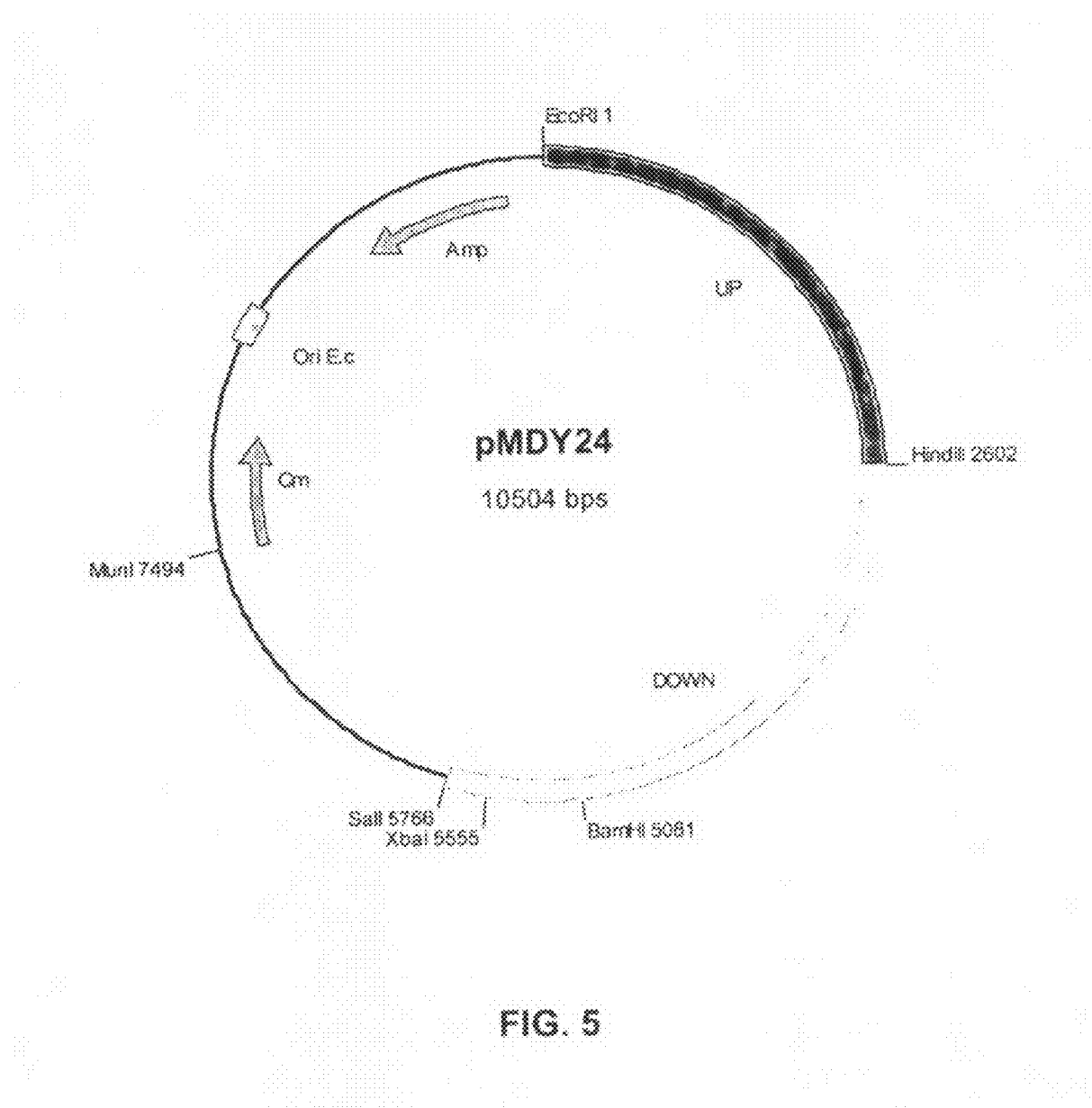
FIG. 5. A restriction endonuclease cleavage site map for pMDY24 showing the location of the chloramphenicol (Cm) and ampicillin (Amp) resistance markers. The Bl0108 flanking sequences are inserted between the EcoRI site (base 1) and the SalI at 5766. The plasmid does not contain an operable on for replication in *Bifidobacterium*.
Figure 6:
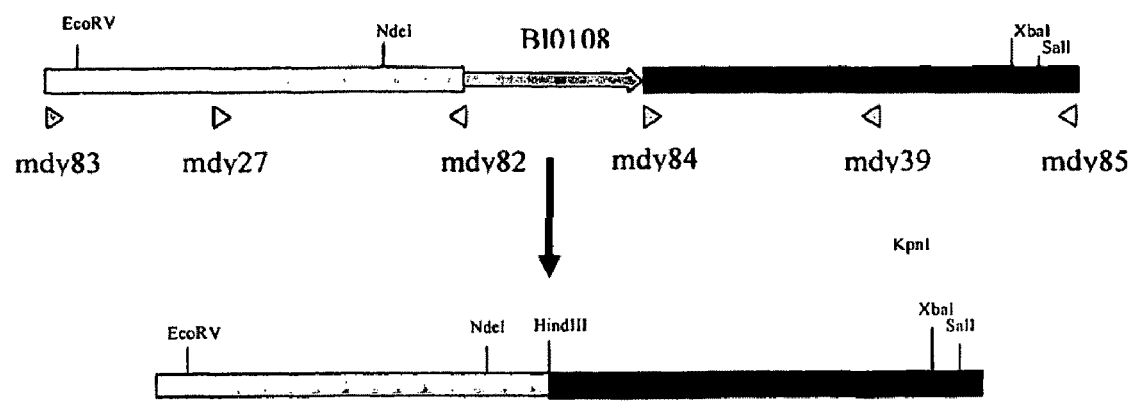
FIG. 6. Map of the Bl0108 loci for NCC 2705 (top panel) and the NCC 9035 (bottom panel) strains, showing the absence of the Bl0108 gene in the latter strain. The Bl0108 flanking sequences used to create the knock-out mutant are shown in the shaded bars in both panels.

The amplified DNA fragments were joined via their common HindIII restriction site and cloned into pJH1101 (Ferrari, F. R. et al., *J. Bacteriol.* (1983) 154:1513-1515) between EcoRI and SalI by a three way ligation. The resultant plasmid was named pMDY24 (SEQ ID NO.:13). A detailed restriction endonuclease site map of pMDY24 is provided as FIG. 5.

Transformation of *B. longum* and Allelic Exchange

Plasmid pMDY24 was transformed into *B. longum* NCC2705 cells in accordance with the method described by Argnani et al. 1996 (*Microbiology;* 142:109-14), except that sucrose was omitted in the growth medium. Cells were spread onto MRS plates containing 3.5 mg chloramphenicol per liter. The resulting cm$^R$ transformants were selected anaerobically. Since the plasmid pMDY24 cannot replicate in *B. longum*, cm$^R$ colonies most likely resulted from the plasmid being integrated into the *B. longum* genome by homologous recombination via a single cross-over event.

The cm$^R$ transformants were cultivated for approximately 100 generations without antibiotic selection to allow loss of the plasmid before individual colonies were plated on MRS agar medium. To ensure that the plasmid was removed from the genome of *B. longum*, individual colonies were tested for loss of chloramphenicol resistance by replica plating on MRS agar with and without chloramphenicol added.

Out of 200 colonies tested, 22 colonies were chloramphenicol sensitive (11%) indicating that the plasmid had been excised from the chromosome of *B. longum* through the occurrence of a second cross over event.

A second cross-over event could result in two genomic configurations:
i) reversion to the wild type configuration with a Bl0108 locus identical to wild type cells, or
ii) deletion of Bl0108.

In order to distinguish between these two possibilities, chromosomal DNA was extracted from 12 out of the 22 chloramphenicol sensitive colonies. The chromosomal DNA was tested for the loss of Bl0108 via PCR with the following primer pair:

```
                                                 (SEQ ID NO.: 14)
mdy27:   5'-TCGGAAGATCTCATGGTCAACGAGTTCGC-3'
and
                                                 (SEQ ID NO.: 15)
mdy39:   5'-TAGTACTAAGCTTCTTGAGCTCTTCCTTCTGC-3'.
```

Figure 7:
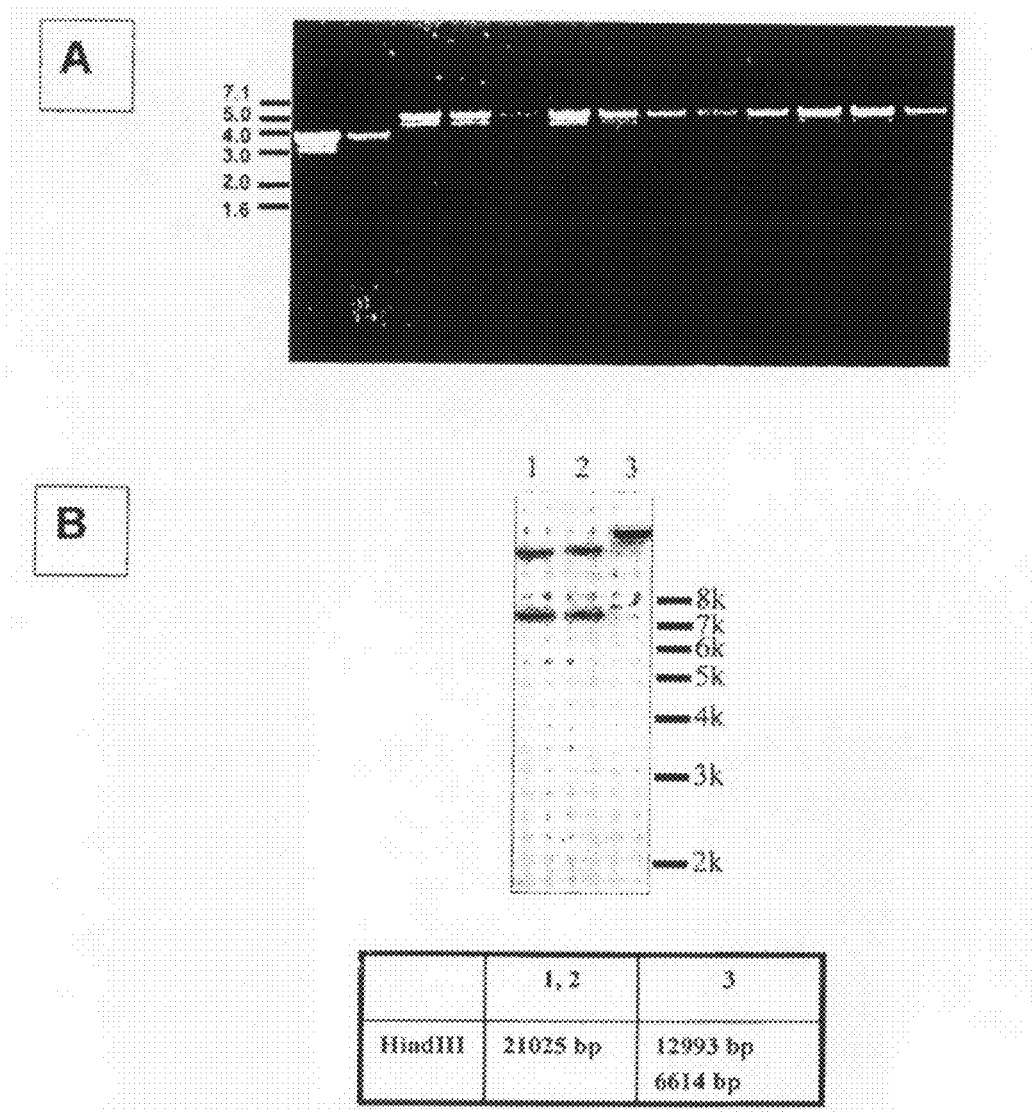
FIG. 7. Panel A shows the PCR analysis of chloramphenicol sensitive colonies obtained after the second recombination event and resolution of the plasmid in the last step of the BL0108 deletion procedure. The size of the PCR fragments from two colonies (lane 1 & 2) indicate deletion of Bl0108 (3885 bp) whereas the size of the PCR fragments from 10 other colonies indicate a wild-type configuration of the Bl0108 locus. Panel B shows the Southern blot analysis for HindIII restriction fragments of genomic DNA taken from two independent mutants (lanes 1 & 2). Lane 3 contains comparable fragments obtained from the wild-type strain (NCC 2705) used to create the mutants. Bottom panel shows the sizes of the fragments observed on the Southern blot obtained for the mutants (1&2) versus those obtained for the wild-type strain (3).
Figure 8:
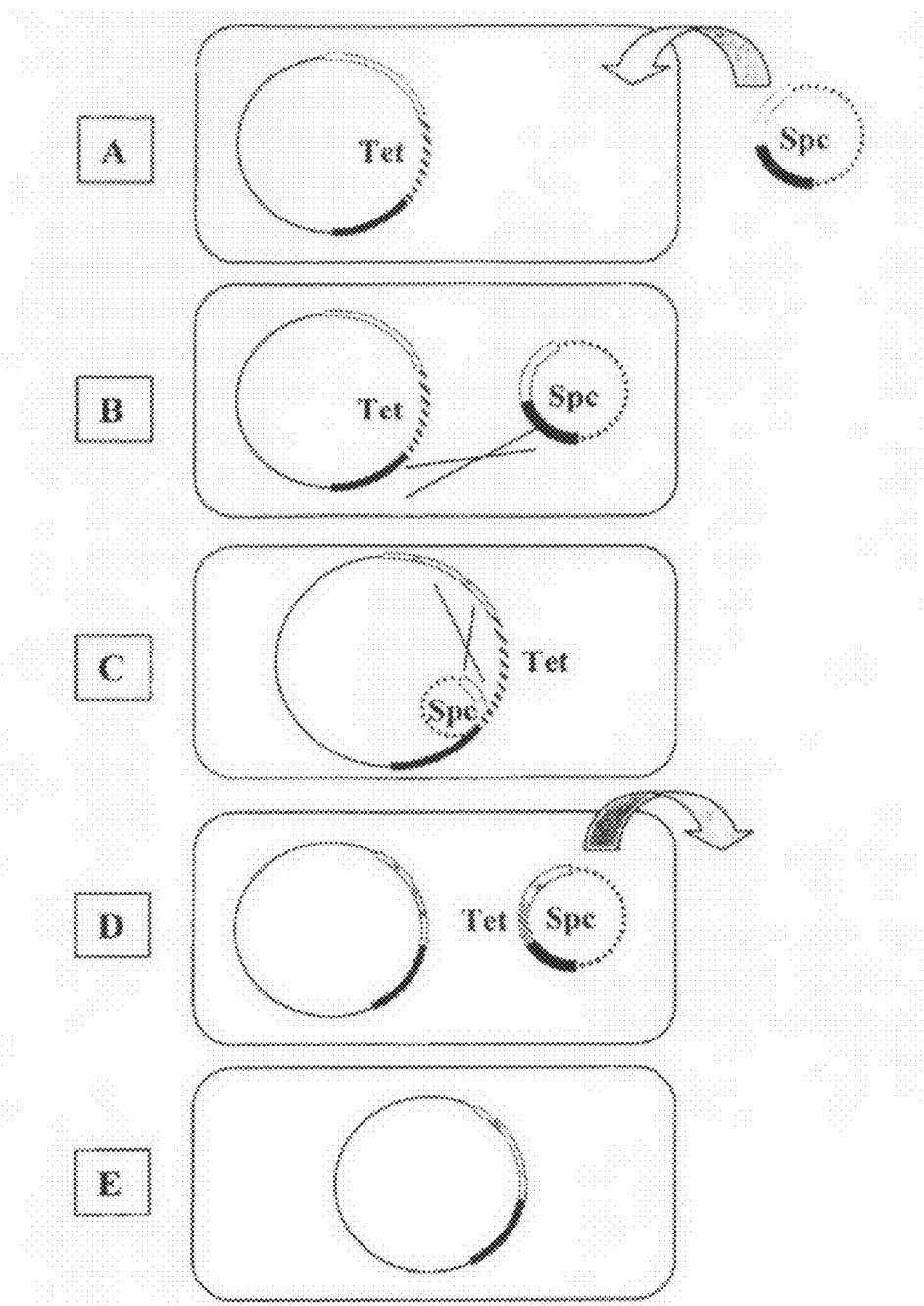
FIG. 8. Schematic of a generalized strategy for deleting a functional gene from a *Bifidobacterium* cell. This strategy in one example of a strategy used in the methods described herein, and in the examples. Briefly, the desired mutated region (in this example the mutated tetW locus) is cloned in an *E. coli* plasmid (A) and transformed into *Bifidobacterium* cells (B). Integration of the plasmid into the genome of *Bifidobacterium* is obtained by homologous recombination and selected by plating cells on growth medium containing the appropriate antibiotic, in this example spectinomycin (C). Cells are replicated without antibiotic selection in order to allow a second event of homologous replication that leads to the resolution of the plasmid (D) and the chromosome region mutated in the same configuration as in the plasmid depicted in panel A. The plasmid, that after allelic exchange harbours the wild-type locus of the region, cannot replicate in *Bifidobacterium* and is eliminated during replication of the cells grown on medium without antibiotic selection (E). The final mutant cells are checked with appropriate molecular biology techniques such as PCR or Southern blot analyses.

Of the 12 colonies tested, two showed a PCR fragment of 3885 bp indicative of a deletion of Bl0108 (FIG. 7, panel A, lanes 1-2) The other ten colonies tested resulted in a higher size PCR fragment of 5311 bp similar to that obtained with wild-type cells (FIG. 7, panel A, lanes 3-12).

Southern Blot Analysis of Bl0108 Deletion Mutants

Deletion of Bl0108 was confirmed by PCR and Southern analysis with genomic DNA extracted from the two candidate mutants identified by PCR analysis as described above, and shown in FIG. 7. Chromosomal DNA samples were digested with restriction enzymes (EcoRI, and HindIII). Southern blots were hybridized with DNA from pMDY24. Southern analysis confirmed that the BL0108 gene had been deleted from the genome of both candidates mutants (FIG. 7, Lanes A&B). Only one strain was retained; it was subsequently designated NCC 9035.

What is claimed is:

1. An isolated *Bifidobacterium animalis* subsp. *lactis* cell comprising a genome that is customized so as to lack an operable functional gene that provides antibiotic resistance, wherein DNA coding for the functional gene is substantially deleted, and wherein the functional gene is tetW.

2. The isolated *Bifidobacterium animalis* subsp. *lactis* cell of claim 1 that is *Bifidobacterium animalis* subsp. *lactis* strain NCC 9034.

3. The isolated *Bifidobacterium animalis* subsp.*lactis* cell of claim 1 that is at least 5 times more sensitive to tetracycline than a comparable cell which contains an operable tetW gene.

4. The isolated *Bifidobacterium animalis* subsp. *lactis* cell of claim 3 that is at least 10 times more sensitive to tetracycline than a comparable cell which contains an operable tetW gene.

5. The isolated *Bifidobacterium animalis* subsp. *lactis* cell of claim 4 that is sensitive to a concentration of tetracycline greater than about 0.3 micrograms per milliter as determined using a disk diffusion assay.

6. The isolated *Bifidobacterium animalis* subsp. *lactis* cell of claim 5 which is *Bifidobacterium animalis* subsp. *lactis* strain NCC 9034.

7. The isolated *Bifidobacterium animalis* subsp. *lactis* cell of claim 1 that is substantially unchanged in a remainder of its genome.

8. A culture of *Bifidobacterium animalis* subsp. *lactis* comprising an isolated cell of claim 7.

9. A method of producing a *Bifidobacterium animalis* subsp. *lactis* cell comprising the steps of:
   obtaining upstream and downstream sequence for a predetermined functional gene from the *Bifidobacterium animalis* subsp. *lactis*;
   transforming a population of the *Bifidobacterium animalis* subsp. *lactis* cells with a plasmid that is nonreplicative in the *Bifidobacterium animalis* subsp. *lactis*, the plasmid comprising the upstream and downstream flanking sequence for the functional gene and a gene encoding a selectable marker;
   growing the *Bifidobacterium animalis* subsp. *lactis* cells under conditions allowing cells containing the gene encoding the selectable marker in the plasmid to grow, but not those cells without the gene encoding the selectable marker to grow, thereby selecting for transformants containing an integrated plasmid;
   growing the transformants under nonselective conditions that allow growth of the cells but permit the loss of the integrated plasmid;
   selecting cells that have lost the integrated plasmid by replica plating colonies onto plates with and without selective pressure and selecting those colonies that are sensitive to the selective pressure; and
   confirming that the cells sensitive to the selective pressure no longer have the function of the functional gene, thereby producing a *Bifidobacterium animalis* subsp. *lactis* cell lacking an operable predetermined functional gene,
   wherein DNA coding for the predetermined functional gene is substantially deleted, and wherein the predetermined functional gene is tetW.

10. The method of claim 9 wherein the selective pressure is the presence of an antibiotic.

11. The method of claim 10 wherein the antibiotic is spectinomycin.

12. The method of claim 9 wherein the plasmid integrates into the genome by homologous recombination.

13. The method of claim 12 wherein the integrated plasmid is lost through a second homologous recombination.

14. The method of claim 9 wherein the transformants are grown under nonselective conditions for at least about 100 generations.

15. The method of claim 9 wherein the *Bifidobacterium* cells that are transformed are *B. animalis* subsp. *lactis* NCC 2818, and the resultant cells are *B. animalis* subsp. *lactis* NCC 9034.

16. The method of claim 12 wherein the only functional gene that is rendered inoperable is the predetermined functional gene.

* * * * *

SEQUENCE LISTING

```
<160> NUMBER OF SEQ ID NOS: 15

<210> SEQ ID NO 1
<211> LENGTH: 26917
<212> TYPE: DNA
<213> ORGANISM: Bifidobacterium animalis

<400> SEQUENCE: 1
agtgatggag acctatgccg accaccgtat ggccaccttc gccgcgatgc tcggattggc      60
gattgatggc attgaagtaa cgaatgtgga gaccacgcgc aagacgattc cggatttcgt     120
gggtatgtgg aatggcatgt tgcgcggcaa gtgacagtag gcgcccggaa aaatgtgagg     180
ggctgcaaga cgaacggtct tgcagcccct cacatttttt gtggagaatc agatcttgtt     240
gccgtaggtg tcttccccgg cggtgacgat ctcgttggcg cgctgtgcga tggcgagctc     300
ctcattggtg gggtagacga cgacggtgac agtggaatcc ggcgtggaga taatgcgcgg     360
ttccttcgaa cgggtgtcgt tcttgtcgtt gtcgagcttg acaccgaacg gtgccagctt     420
ctcacacacc atgcggcgaa cgatttcgtc gttctcgccg acaccggcgg tgaaggtgag     480
cacatcgagg ccgccgagct gtgcggtgta ggcgccgatg tagctgacga tgcggtgcac     540
gtagatgtcg agggcgagct tggcgttctc gtcgccttcc gcaacgaggc ggtgcacttc     600
gcgcatgtcg ccgaagccgg tcatgcccat catgccggac ttcttgttga acaggtcgtc     660
gagctcatcg acattcatat cggcattgcg catcaggtgg aacacggcgg ctggatcgat     720
gtcgcccgtt cgggagccca tgacgaggcc ttcgagcggg gtgaggccca tggaggtctc     780
gatggggcgg ccgccgagtt ccgcggaggc ggaggcgccg ttgccgatgt gcagcacgat     840
ctgcttgagg cccttggcgg cctcggcgtc aatgccgagg aactctggaa tctgggagga     900
gacgaaccag tgcgaggtgc cgtgtgcgcc gtaacgcttg atcttgtact tgtcggcgac     960
ttccttgttc aacgcatagg tgctcgatgc cttcggcagc tgctggaaga aggaggagtc    1020
gaagacataa acctgcggaa tctcagggag cagctcgcgc atgactcgcg cccccttggc    1080
ctccgggccg ttgtgcagcg gagcgagcac agccagctcc tcgaccttgg cagtggtgtc    1140
```

-continued

```
gggggtcacc aaggcagggt tcgggaaggt gtcgccgccc tggacaactc ggtgcccgac      1200
ggcgatgatg ccggtctctt caaggctcgg gccgtattcc tcgaagaacc cgagcacgcg      1260
cttgaggccc tgctcatggt tttcgacctt ctcgtcgagc tcgtgctttt cgccgttgta      1320
ttcgtacttg tagtggccgt caatcggttc gccgatcttc tcgacgatac ccgatgcgat      1380
tccttcgccg gactcgagat ctaccagctg gtacttgatc gagctagaac ccgaattgat      1440
aacaaggacg gttttcgcca ttgtggcatc ctccattggt gattgctctg ccgctatgcg      1500
gctttccaac acacaagatt actcaatgtt tgctacaaaa cggtgaatgg gtgccctctc      1560
gttctatatt tcgaaaaagc acccatccac gtcatgaatt cgcgagatgg tgtggactat      1620
tcgttacttt gcgcttcgat ggcggtcaag gcgatggtat tgatgatgtc ctgcaccaag      1680
gcgcctcggc tcaggtcgtt gacaggccgg ttgagcccct gaagcaccgg tccgatcgcc      1740
acggcgccgg aggtgcgctg cactgccttg tagcagatgt tccccgcatc gaggtccggg      1800
aacacgaaca cggtgacatt gccggcaatc gggttgccga aggccttgac cctggcaacc      1860
gtcttcgacc aagcggcatc gaactggatg ggaccgacga tgggtaggtc cggtcgtttg      1920
ttctgggcga tcgaagtggc ctcgactacc agatcgacat ccggtccctt accgaacccc      1980
aaggtggagt aggagagcaa accgattttg ggatcgatgg agaatgcctt ggcggtctcg      2040
gccgactgga tggcgatgtc ggccagctgc tgcggatcgg gatcgaggtt gatggcacaa      2100
tcggcaaata ccgacacatg gtccttgaga cacatgagga aggcacccga tacggaggag      2160
acaccgggtt tcgtcttgat gagctggagc gcggggcgca cggtgttggc ggtggagctg      2220
atggcacctg agaccagacc atcggccatg ccgagcacga tgagcatggt gccgaagtag      2280
ttcgtgtccc tgagtgtctt cagagccaca tcggggtca tgcccttctt ggcgcgcaat      2340
tcgcacagtt tgggcaccat ggtgtcgagc agatgcttgt cgtcgatgga gacgaacttc      2400
gcctgatcaa cgccttgag gccgagtttt tcaccccggg caagaatctc gttgcggtcg      2460
ccgatgatga ccagatcgac cacattcgac tgcagcaggt agttcgcggc ggtgatgatg      2520
cggtcgtcct ctccttccgg tagcacaatc gtcttcttgt ctttcttcgc acgtgcgagc      2580
agatcgtact ggaacgcgaa tggtgtggtc ggcggtacga aaggtgtgtc aagcacgttg      2640
aggagtgatt ccttgtcgac atgctcgtcg aaggcatcga gcgcggcctt gacattcgtg      2700
tcagcggaac cgagttccac gaggggaagc ggccacgtcg gcaggtcgta gctcacgaat      2760
tcgtcggtga gtgtgggcag cgccgaattc gtgcagtcgg tgatgaacac gccgatcact      2820
tgggtgcctg cgttggcgac cacctcgcgg catgcgtcta tcgtctcacg aatctcgtcc      2880
ggcgtgcgtc ccatcgagct cactgagagc agcaccggag actgcaggtc ggcggagacg      2940
tccgcattga aggtgaaccg ttcgggatcg cccacattgg tgcggtctga tccgacgatc      3000
actcggatct gcggattgat ctcggcattc gtgtcgatga atttggagac gatctgctgg      3060
cgggcattgt ctttgtcaag acgtgcgtca tgcagtgtga cgccgacggc ctgttcgcgc      3120
gtctgcagca cgctcaccac cgagaggagt gcatcggtga gattttcgtc tgcctgcacc      3180
gccggtcgga atatgctggt cttcgcgtg tgggcgagca tatccaccac acccaatgcc      3240
accacgttcc ggccgtctcc aggttcggga ctgatgatgc tcacgttttt gaggctcacg      3300
atgactcctt tgaaatcgat gatctgcctg acgtgcgact gcgttgtgca cgcagaccat      3360
tgtaactggg aagggggcgt ggcagaccgg ttattttgca attgccacga gaatgtgacg      3420
caggtcacat tctgtatggg tatgggatat tcggcgttgt gtgatggata gcaaatggat      3480
agcaaaaggc ccgggtgctg acacccgggc cttcatcgg ctaagcgatg agactatgct      3540
```

```
cactcgttgt cgccggcggt cgcggcggtg gcggagagca tggaggtctc gtcgaccttg    3600
acatccgggt acacccaatc ggtgaactca ggaatgtcat agccattgtc gacggcgaac    3660
tggaacgcgg tcttgcggaa ctcgttgagc tcgttgatct tgtcggcata cttgtcggcg    3720
tcgatgagct cgagggcctt ggcctgaagg gcgtagcgat ccatgtcgtt gacacgcacc    3780
atgtcgaacg gcgtcgtcgt ggagccctgc tccttgtatc cgacaacggt gaagttgtcg    3840
tggttcgggc ggtcgtagat gaggccacga acgtcctggg cataggagtg gtaggcgaag    3900
aggaccggct tgtccgcggt gaacaggtcg gcgaagtcct cgtcagacat ggcctcgtcg    3960
ttctccttcg aggactgcag cttgatgagg tccacgacgt tgacgacctt gaacttgatg    4020
cccatcttgt tgagggcatc ggaagcggcc atgatctcct gggtcgggac gtcgccggcg    4080
gcggcgagga caacctggac ctcgtcgttg ctcttggcct tggaagccca cttccactcg    4140
gcggcaccag cctcgagctc ggcgcgtgcc tcgtcgaggg tgatccacgt cgcggccggc    4200
tgcttgccgg cgaagattgc gttgatcttg ttggtggact tgaagcactt ctcggcgatg    4260
gccagcagca tgttggcatc ggtcgcgaag tagatgttcg tcacgtggtc gttgttgaac    4320
gtcttgttca gcaggacgga ggtcacaccc ggatcctggt gcgagaagcc gttgtgatcc    4380
tgacgccaca cgtgcgagga gaccaggagg ttcaccgagg agatcggctt acgccacggg    4440
atctcgcgga cggtggcctc gagccacttc gcatgctggt tcagcatgga gtcgatcacg    4500
tgcacgaagg actcgtagga gctccagatg ccgtgacggc cggtgagcag gtaggcctcg    4560
aggaagcctt cgcactgatg ctcggagagc tgctcgacaa cctggccggt gacggccatg    4620
ttctcgtcga cgagagccga gaggtatccg ttgtcccact gcttcttggt gacctcgtag    4680
gtcgcgttca cacggttgga cgcggtctcg tcaggtccga agacgcggaa cgaatccggg    4740
ttgttcttga tgatgtcgcg gcagtacgcg ccgagggaac gcggagcctc gacctggccc    4800
caaccgtggc cgtattcctt gacgccggtg atctcgtact gatcgagctc agggagcttc    4860
agatcctcgc ggatgcggcc gccgttggca ttcgggttgg cgccgatgcg cagttcgccc    4920
ttaggcatga atgcggtgac gtcctccttg atggagccgt cggcgttgaa gagctcctcc    4980
ggcttgtagg attccatcca gcccttgagg acttcgaagt gggcctcggt gtcgcgggcg    5040
gaagccagcg ggacctggtg tgcacgccag gagccttcgg tcttcttgcc gtcgatgaac    5100
ttcgggcagg tccagccctt cggggtgcgg aagatgagca tcgggtagaa cggacgggtc    5160
atgtcgtcgg tctgagccgc agccttgata tcgcagatct cgtcgaagat ggtctcgaag    5220
agctcggcga agcgacggtg gatcgacagg tgatcctcgt tgtcgaagcc ggcgacgaac    5280
tcgtacgggt ggtaacccat gccgcggaag aagtcgtgca gctcctcgtc ggagatgcgg    5340
gcgaggatcg tcgggttggc gatcttgtag ccgttgaggt gcaggatcgg caggacgatg    5400
ccgtcggtgc gcgggttgac gagcttgttg gactgccagc cggtggccag agggccggtc    5460
tcggcttcgc cgtcaccgat gatgcacggg acgaagaggc tcgggttgtc catgatcgcg    5520
ccgtaggcgt gcgacagggc gtagcccagc tcgccgcctt cgtggatgga gcccggcgtc    5580
tccggagcga agtgggaagg aatgccaccc gggtaggaga actggcggaa gaacttctgc    5640
aggccagctt cgtccttggt gatgttcggg tagtactcgg tgtaggtgcc gtcgatgtag    5700
gactgagcgg tacctgcagg gccgccgtgg ccaggaccca tgatgaacac ggtgttctgc    5760
tggtgatcgg cgatcaggcg gttgatgtgg gcgagaagga agttcaggcc cggggtggtg    5820
ccccagtggc cgaccagacg gtgcttcacg tcatcgcggg tgaagggctc cttcatcagc    5880
gggttgctac gcaggtagat ctggccgata gacatgtagt tggcgacgcg ccagtacttg    5940
```

```
tccatgcctt cgatggcctc ttcggaaacc ggacgatcca gcttctgcca tggggtacca    6000
ataacaggat tagtcatgtg tgctcctgta ctcctgcaca taaatgtgcg atttgtttat    6060
tccgttgggc acgggcttcg gcgctgtcct gcaggccggt ctccgtgccc gatcgctgat    6120
tatgttacgc gaatacgctg accttttgc agttttgaa acagtgtgag cgaatctgtg      6180
cgcataattt gcgaatttgg gagattgctc gggcgatttg tgaaaatgga aaatcagtga    6240
ataaaggcga gaaacgttga ataccaacg aatgcaagcg ttttcgccgt cgttgtcgcg     6300
tgcggtttgt gaggatattg cgcggcgtgt tgaaaacaag cgaacaatct ggaaaatcct    6360
tgtgattgca gtgcttgagc gcttaagacg acaccgatgc gacccgtggc atgtgcgaat    6420
ttcaatgtct acttgcctgc gcacaataga tgtgttgtaa tgcccgagta atgaacctat    6480
atataagggg agcgtaatgg cagcaggtcc tgtccttgtc gttgatttcg gagcgcagta    6540
cgcgcagctc atcgcgcgcc gcgtgcgcga ggcgaacgtg tattccgaat tggtgcctca    6600
ttcgatgccg tcgaggaga tgctggccaa gaagccgtcc gcgatcatac tgtcaggcgg     6660
cccggcgtcg gtgtacgaac ccggtgctcc caccattgac aagagcatct tcacggccgg    6720
agtgccggtg cttggcatct gctatggctt ccaggtgatg gcccatgagc tcggcggcga    6780
cgtcgacaag gcggcgctcg gcgagtacgg caagacggag gcggtggtgg acgatgccac    6840
gggcattctc gacagttcgc catccctgca gaccacttgg atgagccatg gtgtcgccgt    6900
gaacaaggca cccgccggat tcgaagtcac cgcgcatacc gaaggggcgc cggtggctgc    6960
gatggaggat ccctcacgca aactctacgg cgtgcagtgg catcctgagg tcaagcacac    7020
gccgttggga caggatctga tcgagaattt cctgcatgat tgcgccggca tcgaagccga    7080
ttggaacgca aggaacatca tcgacgagca ggtcgctgcg attcgtgaga aggtcggtga    7140
cgcacgggtc atctgtggtc tgtctggtgg agtcgattcg gccgtggctg cagcgctcgt    7200
gcaccgcgcg atcggtgacc agctcacctg cgtgttcgtg gatcacgtc tgctacgcaa     7260 gggcgaggcc gagcaggtca acatgatttt cgtcgcggcg accggcatca gctcatcgc     7320 cgtcgatgcc tccaaggatt tcctcgatgc actcaagggc gtctccgatc ctgagacgaa    7380
gcgcaagatc atcggcgaaa aattcatccg cactttcgag aaggcgcagc gccaggtgat    7440
agaggaggcc ggtgcccagg gcaaggaggt caagttcctc gtgcagggca cgctttaccc    7500
ggacgtcgtc gaatccggtg gcggcgacgg cgcctcgaac atcaagtcgc atcataacgt    7560
cggtggtttg cctgacgaca tcaagttcga actgattgag ccgctccgtt cgctgttcaa    7620
agacgaggtg cgcgccatcg gcaccgaact cggcttgccg gacgagattg tctggcgtca    7680
accgttcccc gggccgggtc tgggcatccg catcatcggt gagatcacga aggaacgtct    7740
cgacttgctg cgtgatgccg atgcgattgc ccgcgaggag ctctcgaagg ccggtctcga    7800
ccgcgacatc tggcagtgcc cggtcgtgct gctcgccgac gtgcactccg tcggcgtgca    7860
gggcgacgaa cgcacctacg gttcgccgat cgtgctgcgg ccggtcagct ctgaggacgc    7920
gatgactgcc gactggtcgc gtgtgccgta cgacgtgctc gccaccatct cgactcgcat    7980
cacgaacgaa tgccgtcaga tcaaccgcgt tgtgctcgac tgcacgtcga agccaccggc    8040
gacaatcgag tgggaataac tgacaaaacc cgcaaagcct tgaaaacact ggggtcttaa    8100
agcggaaacg gggcatttga tagcaaattg atagcagata ccaaaaccgg atttactttg    8160
ttcactcccg tataacgggt ggcttgcggg taaatcctcc atatcctaag aaaaaggtct    8220
tgctgacttt caccagtcgg caagacctt tttgttattt gtcttttctc tgtttcttca     8280
atccttttat cagagcatcg cttaattcct tcgagggac tttggcccac cgctgggtgg     8340
```

```
tgtcgtactt cgggtagttg tagcgccagc ggtcatagtc ctccttggtg atctccccgg    8400
cctccaactt cgccgcctgt tcccgccacg caatcaagat tttgttcagc tcactggctt    8460
gacggcctcc ctgaaaaata tctgcttgca ggcaggcacg tccatccgcc tctaccactt    8520
tcagactgta aacatcctcc aaggcgaaca gcgtatgggc caaacctatg tagttgtcta    8580
tgtccgggac gctcaacgcc tggggcgata catctaaggc aataccgcac agaaaaaaag    8640
tgccatatat cgccaagtgt gatataacaa acttatggat aaacagatga cgatttccgc    8700
attcagcgac gaactggcac aggtgcggac gaagaaaaaa gcatttctcg accagattga    8760
acggatcgtc ccgtggaagg aatggcttgc catgattcag ccgtgctatt acaaaggaga    8820
gcgcggcaac aaaccctatc cgctggagat catgctccga ctgtatctgc tgcaaaacct    8880
ctatgacctg agtgacgagg ccacggtggc agaagccatc gacagccgcg catttcggga    8940
gttctgcggc gtcgattcca gcaaccaggt tccgaacggg gatactcttg gccggttccg    9000
gaacttgctg atcaagaacg gactgcagga gaagctgttc gctcaggtgg tagcagcgct    9060
catggaacgt ggcctcattc tgaaaagggg caccattgta gattccacca tcatttccgc    9120
cccctcttct accaagaata aggaaaagaa acgggatccg gatgcccacc aagtcaagaa    9180
gggcaacacc tggcactttg gtacaaagc gcatatcggc gtggacaagg acagcggact    9240
ggttcacaca gtggaagcta caccggcaaa tgtccacgac gttgcggaag tgccgaaatt    9300
attgacggga gaggaagaaa cagtctatgg agacagcggt tatctcggcg caggtaagcg    9360
cgaagatgcc gtagtccgaa acaaagctgg ccggaaaatc aagtacaaga tcaatcgtcg    9420
tccatcgcag atgaagaaac tgagcaaaag cgggcagtac gcagcaaaga aagcggaacg    9480
ggcgaaatcc tcagtgcgag caaaagtaga gcatgtattc ggtgtcgtta agaagcagct    9540
gcgcttccga aaaacgcgat accgagggct tgaaaagcaa caagccaaat tcaatatcat    9600
gtttgcgttg gcaaatctga ttctggctga cagaccctgt ctggcagctt gagtcagtgc    9660
gccttttgcg g acaaaaaatt cggaggttat ccacagtttt tattcggcac ctgctgtata    9720
atgcggattg tggcatttgt gcggtgttgc cttaaataaa actataatca aatagtggga    9780
acaaaggatt atgatagtcc cttttgtagg ggcttagttt tttgtaccca atttaagaat    9840
acttttgcct tatcaatttt gacatatccc caaaaacagc actcacaaac aggtgtatgc    9900
tgtatatgtg tatgtccgca aattatcatc cccagtggta aaagtatttt actgctgggg    9960 attttttatgc ccttcggggc agtaaaggga ggacaatcac atgaaaataa tcaatattgg   10020
aattcttgcc catgtagacg ctggaaagac gaccttgacg gagagcctgc tatatgccag   10080
cggagccatt tcagaaccgg ggagcgtcga aaaagggaca acgaggacgg acaccatgct   10140
tttggagcgg cagcgtggga ttaccattca gccggcagtc acttccttcc agtgcacag   10200 atgtaaagtc aacattgtgg atacgcccgg ccacatggat tttttggcgg aggtgtaccg   10260
ctctttggct gttttagatg gggccatctt ggtgatctcc gctaaagatg gcgtgcaggc   10320
ccagacccgt attctgttcc atgccctgcg gaaaatgaac attcccaccg ttatctttat   10380
caacaagatc gaccaggctg cgttgattt gcagagcgtg gttcagtctg ttcgggataa   10440
gctctccgcc gatattatca tcaagcagac ggtgtcgctg tccccggaaa tagtcctgga   10500
ggaaaatacc gacatagaag catgggatgc ggtcatcgaa ataacgata aattattgga   10560 aaagtatatc gcaggagaac caatcagccg ggaaaaactt gtgcgggagg aacagcggcg   10620
ggttcaagac gcctccctgt tcccggtcta ttatggcagc gccaaaaagg gccttggcat   10680
tcaaccgttg atggatgcgg tgacagggct gttccaaccg attggggaac aggggagcgc   10740
```

```
cgccctatgc ggcagcgttt tcaaggtgga gtatacagat tgcggccagc ggcgtgtcta   10800
tctacggcta tacagcggaa cgctgcgcct gcgggatacg gtggccctgg ccggagaga    10860 aaagctgaaa atcacagaga tgcgtattcc atccaaaggg gaaattgttc ggacagacac   10920
cgcttatccg ggtgaaattg ttatccttcc cagcgcacag cgtgaggttaa acgatgtatt   10980 aggggaccca acccggctcc ctcgtaaaag gtggcgtgag gaccccctcc ccatgctgcg   11040
gacgtcgatt gcgccgaaaa cggcagcgca agagaacgg ctgctggacg ctcttacgca    11100
acttgcggat actgacccgc ttttgcgctg cgaggtggat tccatcaccc atgagatcat   11160
tctttctttt ttgggccggg tgcagttgga ggttgtttcc gctttgctgt cggaaaaata   11220
caagcttgaa acagtggtaa aggaacccac cgtcatttat atggagcggc cgctcaaagc   11280
agccagccac accatccata tcgaggtgcc gcccaacccg ttttgggcat ccatcggact   11340
gtctgttaca ccactcccgc ttggctccgg tgtacaatac aagagccggg tttcgctggg   11400
atacttgaac cagagttttc aaaacgctgt cagggatggt atccgttacg ggctggagca   11460
gggcttgttc ggctggaacg taacggactg taagatttgc tttgaatacg ggctttatta   11520
cagtccggtc agcacgccgg cggacttccg ctcattggcc ccgattgtat tggaacaggc   11580
attgaaggaa tcagggacgc aactgctgga accttatctc tccttcaccc tctatgcgcc   11640 ccggaatat ctttccaggg cttatcatga tgcaccgaaa tactgtgcca ccatcgaaac    11700
ggtccaggta aaaaaggatg aagttgtctt tactggcgag attcccgccc gctgtataca   11760
ggcataccgt actgatctgg ccttttacac caacgggcag agcgtatgcc ttacagaact   11820
gaaagggtat caggccgctg tcggcaagcc agtcatccag ccccgccgtc caaacagccg   11880
cctggacaag gtgcgccata tgttcagtaa gatcacttga tacaccacag cgaggaaggt   11940
tattgcattt ccctgtcttt cgtggtaaaa tgtagttgta aaccaccaga gaaaccaatc   12000
taattttacc gttgatagcc atttccttga tagccaaatg atagcaaaag ttcggcaagc   12060
ccataggata aggataatag gtatcaggaa aaatcaaatg atatcaaatc tcccaaacaa   12120
aagcgtttag aattaagttt cattttgcga atgggagtga ccccgccgat catgcgacca   12180
tcgctcccat agcgtctttc tttgcaggtg gcgcccgccg aagcctatct tcggcgggcg   12240
ccacctgtcg tcgttctgct atccagtatc cagtttcttc tcatggaagg tgccccggac   12300
gacgattacg acgtggacat cgatttggat gcgggcttca aggtgggacg ccatgacgtc   12360
gaatccatcc gaagacccga accgggacgc ctcccaaggg gagggggaa tgcgatccgt    12420 atccgctaga agcgcgcccg cagtcgatag ggcaaatcat gaacatgtga ccggcaccgg   12480
aaagtgacat aatccgattg tcggcaatgg gctcgatatg gtatcagccg agcagccagt   12540
cgacgatatt gcgtatctca atgccgtcag aggtcgtgcc gagacggaat ctgtcgagtg   12600
tgagcacgat tttcgggaat gcatccgata acgattgcaa aggcgcgagt tccctcgcgc   12660
gggtggattc ttcgagcatc gtcccggtga cctgaatgta gattctcctg tcgaatcgtt   12720
gagcgacgaa atcgatttca cctccacgca gactgccgac atgcacgttg tacccgcgtc   12780
tgcgcagctc gttcgcgacg acgttctcca attggaatcc gtagttttgt gaggagaaac   12840
catttgcgat gttgcatagt ccggggtctt cggcgtggaa cttgcgatgt gtcacaaacc   12900
gctgaaggtg tcaggtataa ctgacatttc tcggatttca agatggtttg tcgggtataa   12960
ctgacggatc tgtttgaggg tgcatcccgt aagaaagtgc agccggtaag tggatataga   13020
ggatatgggg tataccggttg caggaagcga gtgaatgggg tgtgatgatc gacaaccatg   13080
gatgcggtta cgggatacag tggtatgcgc cgtgtgcttg tcatcggatg tccgggtgca   13140
```

```
ggcaaaagca cgttcgcgcg caggttgcgg gatgcggccg gactgccgct gcattatctg   13200
gacatgctgt ggcacaatcc ggaccggacg actgtcacac gggccgaatt cgatgagcgg   13260
ttgcaaagga tcctcgagga ggatgcctgg atcctcgacg gcaatttcgc gcggacgctg   13320
ccgaaacgac tggaatattg cgacaccgtg ttcttcctcg acttcccgac cgacgtatgt   13380
cttgagggcg tcgagggatg tagcggtatg aagcgcgaag acatgccgtg ggtcgaacac   13440
gaattcgatg aggagttccg tcagtacatc atcgactttc ccgctgagcg cgtccgcag   13500
atggttgacg cgcttgaaga cgccgccgcg cgccgcggtg tgcgtgtcca taccacatcc   13560
aaggcagagc tggtgcaagc gctcgctgat gttttgagtg gtcttgaagt ggggcgggcc   13620
agagcatgtc tgacgttcat catgtaccgt tatgcgacat actgggcatc acggtgaacg   13680
aactgcttgg tgggggagga acttacaaaa gtggattccc gtcagctcca tcctccgtcg   13740
tctcatcgta tgcgagcgcg agggcaccat cgtctcctca tgtgtatgcg tcatcatccc   13800
gaatctgacg cggggtgtgc ggccatacgc gttcgtcgag aacgtcgtga cgcgcgccga   13860
tgcgcgtggg catggttatg ctaccgcatg tctgaaccat gcgaaggcgc tcgcgcagca   13920
ggccggctgc tacaagatga tgctgctcac cggctcccat gatccgaaga cactcgattt   13980
ctaccgccac gccggctaca gcagcaccga caagaccgcg ttcatccagt ggctgtaggg   14040
cgcgtccgtg tcacggtatc gcatccacca ccgtcgatat ccgtttggca tcgctcgacg   14100
gcgggatgat gtggctgtca accggaagtg aacgtaggat gcgcagctcc cgctctctgc   14160
gctcttcaag gcacgcgata taccctcat atccgcgcaa cccatgcgct tcaccgtacc   14220
cttgtgctgt gtggtagtcg atgacggcat tgagccaacc atcaccgcgt tcgtcgagga   14280
caccgtcaat cgccgatttc gcgcccggtt cgtcaatgta gatgacgacg ggatgcagtg   14340
gcgcgatgat cgccgcaata tcgctgatgt accgtcgtga ctcgtcctcg ctcatgccga   14400
accgcatcat cgtctcgcac atcggattct gcagcaggac gcaattgaat acataggtcg   14460
tatcaggttc ggcgtgggct gcgaacgcgc gccaagtatc gagtatcgtg gcgcgttcac   14520
ttgcgaaatc agggaagtcg tggtcgccga catcggcggg atggtctgcg gctccttctt   14580
cgacgcagac gacgttcctt ccgcgcgctt ccaattcggc ggcaaccatc gcagccgtcg   14640
tgcttttccc gctatctggc agcccttcga cgatgatcag acgggttcgc atctcatatg   14700
tgctcatgat gtcatggtac ggcgaaggat atgtgggatg tgcagatgtc catgtatata   14760
gggtgatata accgaatata aggtgatata tagtgatata tcgaaatgaa acgatataca   14820
actcgctcgg gagcatgttg tcgtctttta tgaattcatg atagatctgg aggaatcgtt   14880
gttttgagtc catggatggt cgatgcgctc aagcgcatgt gctggtgcgc gtcgaacata   14940
tgaggccggt gaatgatatg ccgtatgccg cttcttacgc ctcagcgggt gtcggtgatg   15000
gatggtcatg gaactcccgc atctccatat tgatgaatct gctgattatc tcgcgataga   15060
tcgcctcaac cacatccgga ttcgcgccga aacgctcggc cttacctcgc accttcgcga   15120
tgacccgctc catacggttg gtgtcacgta cgccttcctc atctttcttg aatgccgatg   15180
cttgcacggc atattggcct cgtccaccga tcaatgcgat ggtctggtca tcgatggcgt   15240
cgatgtgcga acgcacttcg tccagactgt tgcactgcac ggcggtctcc tcttataagt   15300
ggggattacg gaagatacaa caaaacatgc cgatatggat tgctattcga taccataacc   15360
ttatgcaacg agcacaagca gagacgcttc gatgctctgg gaacagttc attcggctca   15420
cacgcgatga atgtgcgcgc ggtatggcat gctccttgcg gcggttactg cgcgcatcct   15480
tggaaaccgg caacccatac tatggtgctg aatcatgact agtccaagca ttcttcctga   15540
```

```
tgatccgtcg ttgtgcattc ctcccatgga atccgacgat gaaaacgagc tgaacagcca   15600
gaccgcgcat aaccgagcca tggtcgagta ttccgcgcgc tgcggttgtt ccactgcgg    15660 tggcatattc gcagggaacg aagttgcaca atggctgcag gaggacgacg gcgaggacac   15720
tgcgttgtgc ccgtattgtg gcgtcgatgc agtgattgtg ggcaatgaac aatacccggt   15780
atgcatgatg gtgctgagca aactgtatat gcattggttt ggcaaggaat ataggcaacg   15840
tcttgaggct gccactgata tgcccacatg tggcagtcac ggggattatc tgcgcaaggg   15900
ccttccttct ttgacgaatc acgacaggaa aatcacggtg gtcggggaga tcgaactgtt   15960
cccattgtcc gtgtatgaca gggcagagga actgtgcaat gagagccatc ctccacgacc   16020
ggttgaatat gatgacgtgg acgtctacat gggcggcgtg gtgaccgtgc atgcgggatt   16080
cgatgaacac ggatattatt actgtgattt catcaccggc agtggcgtca agctgcctta   16140
cgatgcttgg aacgacgtac agcaggatct ggtgttgaat ctcagcagac aatatggcga   16200
tgcgctgcgc ggaatcatca ctgattcatt gatgcatcac atgcgattgt tcattgatgt   16260
ggatgtagcg gaatgattag agcccatgtt gtgtccgcca tgtggcaagc tgcgcatgga   16320
gctgtgtctt gcggtcatcc gaggcgaacg atgcgtcgat ggagttcttg gcagcgatg    16380 ccaattcctc catcgacata ccgatgtcgg cgagcgcggc atagttcgcc gcggcatagc   16440
ctccgaaata tgcggggtca tccgagttga tcgtgcatac gaccccttca tgcaggaatc   16500
tgggaatcgg atgctcgcgc atgtcgtgta cgacctgcag cctgaggttg acaacgggc    16560 agcaggtgag cggaacgccg tcgcgtgcga cgcgctcgag cagctcgcgg tcgtcttgaa   16620
tgtggatgcc gtggtcgatg cgctcggcgt gcagcagatt gagcgcatcg cggatatacg   16680
ccgccgggcc ctcctcgccg gcgtgcgcca cgcaatgcca gccaaagtcc cttgcccgcg   16740
cgaactgatc gatgaattcg gccggtgggt agccgacttc cgccgaatcg agcccgatgc   16800
cgagaatctc ggttttttcgc ggcgccgcca tgtcgaggat ccggttcgcc gaatcgatat   16860
ccatgtcgcg tacgatgctc agaatcagac cgccgctgat gtcgaagcgc tcccgtccga   16920
tttccaatcc ctcaagaagg ccgtcgagca ccatgtcgaa atccaatccg ttcgtgcaca   16980
catgcacttg cggatcgaag aagatctccg catgccttac cccgttcgca ttcgcccgtg   17040
tgagataggc gagcatgaga tccttaaaat cgtccttggt cttcagcgtc ttcatcagcg   17100
catagtagag ctcgaggaac gactgcagat tctcgaattc atactgcgct cgcaggccgt   17160
cgatatccgt ccacggcaat gtcactccat tgcggtccgc cagcgtcagt gcaagctccg   17220
gttcgagcgt tccctcgata tgcagatgca gttcgctttt cggcatcgtc tccagtgcct   17280
gcctgatttt cccgtccacc atgttcctcg ttccattgcg atatcggttt ccaatattct   17340
acccactcca tgttgtgccg gggcgccgtt cagacggatt tggtggattt gatgagtcct   17400
gtgacaatcg aggcgattgc gcagaggaaa ccgccgatca cccaggacat ccagaacatg   17460
ccgtgcggtc caccgtcaaa gcagaacagc aacgtgaggc cgactatggg ggccgtgatc   17520
atgatgatgc cgcataccgc tccgttcccc ttgtcgtaga ttgactccgt cccattctcc   17580
tgcacgtgtt gctcctccga ttccttgttg tagtcggcga tgtcgagccg cccatactgc   17640
atgccgccga atacgatgca ccacacgccg accgcgacga acatgaggag cgccgtactg   17700
ggccagccct cgtctacgtg gagcgtctca tcggcccata cgttgacggc gatgccggcc   17760
atgatgagcg cgatgcctgc gatcagtgcg atcgcgagca ccttgcgggc ggcggcacgg   17820
tccgactcgg tatagaagtc ctcaacatag ggatgctgac gtttgaacgc gctgtgtgcc   17880
agaccggcgg gaatgagcag ggcgagaccg acgagcgtgc ctatgcgat gcacaggaac    17940
```

```
atcgccacct cattcgcatc gctgttgccc agaatcgaat tgtccgaatc gaacaggttg   18000
ccgatgctga cgccgaagat gatggctgac actcccgtgg gaatcatcag gtcgaatttg   18060
cgcatgtgct cctcgtagcc ggtgatgtcc tgaggcaacg ccgacccttc catctcaggc   18120
atcggtgctt tgggagccca tcctcgaca tgattcgccg acatggcaat tccattgcgc    18180
acgtcaccca tgaccagatc atcgagactc acgccgaaca tatcgcatag catgagcagc   18240
ttgtccattt cggggtacgc cttctcgctt tcccacttgc tcacggattg tcgtgacacg   18300
ccaatcagca ttgccagctg ctcctgcgtc atattgtgcg atccacgcag atactgcaga   18360
ttgtctttga agcccatggt cctgtccttt tccttcgcgc ctactcgttt cggcaaccgt   18420
cgcgggtgcc gatgccccta ctatgcccga aatgcggaaa gcgcgccacc aacttgcggt   18480
tgcatttgct ccgacaaccg gcgatctgat gtcaacttgc ggttgcattg ctggaattcc   18540
aatgattgtt cacgtctttc atcatcgtgt ccacatctcg tcatatggaa tgtcgcgcaa   18600
tatgtctgtg aacatgcctg tgagccaaca cgacagagat atgcactgtt ctatctgtta   18660
tatactgtta tatatcgagc ttggacacat tgtattctcg cgttcgaaag gaggggagat   18720
gcagcttctg atcagtacca cgtcgatgac gccaatctat gaacagattg tcgatcagat   18780
tcgtgcactc atcaaagagg ggagactcaa ggcagggag ccgctggatt cggttcgctc    18840
cctcgctcgt acctgcagaa tctccgcact gacggtgaag aaagcgtacg acgtgcttga   18900
acgggaggga ctcgtcgtca ccgttcaggg caagggcagc tttgtcgcgc agatctcgcc   18960
gaacatcgtc gccgaggagc tcaaccgcca ggtcgaggag caattcgcgc aggctatcgc   19020
caaagcccgg cggcttgggc tgacccgcga ggagatcctc gagcttgtcg tcatgctgct   19080
tgaagacacc tccgcggatt cgggcgacgc ccccgaaggg actgaaggag catcatgaag   19140
attgcacttg accatgtgac gaagcactac ccggatttcg acctcgacgt gacgatggag   19200
gtgccggacg acaccatcac cgctctcatc ggtaccaacg gctccggcaa gaccaccaca   19260
ttcaggctca tgctcggact tgcgaggccg gctggagggg aggggatcat tctcggtgat   19320
cccatccgcc gggtgtgggt gaacgcgaaa tcgcgcaccg gcgtcacctt cggcgacagc   19380
acgttcgtgc cgaccttcac gctgaacgat gagatcgccg aacgcaaacg cttctatacg   19440
acattcgacg aacaatggtg cagggcacag ctgcagaggt tcacgcttcc gctgaaccag   19500
cagattcagg aattctccgc gggcatgctt gccgaatgca aaacgatcat ggcaatggca   19560
catcaccccg aaccactgat cctcgatgag ccgacggccg gtctggacgt catcgcccgt   19620
aacgaagtgc tcgacctgct ccgcgaatac atggagatcc caggccgttc aatgctcatc   19680
agctcgcacg tcgccaccga cctggagaat ctgtgcgacg acctctacct cattgaccgc   19740
ggccgaatcc gcatgcacga gaccatcgat gcattgcacg atgaatatgc ggtgctcacg   19800
ctcaccgacg atcagatgtc agctgcagac ccacggtaca tactcgtcaa acagcgcacg   19860
gccggcggct ggaaagccat taccgacgaa cgcggattct atgaggagaa cttgcccgga   19920
gtggggatct gtggggcgag catcgatgag atcatcacgc tgatgagtgc cgacccgcga   19980
accacaacga tgcaggaaag gacaatgcaa tgaaaggtct gttcgtcaga gacgcaatct   20040
ggcttggcaa gcaacgcatg ctgctggtgt gcatgctggc gttgaccgtg ttctacctat   20100
tctccgacct ccatgcattc ggtgtggcat tcctgccgct catgctggca atgctggtat   20160
gcaggacagt gcagaacgac gtgtcacggg catgtcggcg catgttcttc acgatgccat   20220
ttaatacccg tgattatctc atcgagaaat actgtggcgc catcatccct ccgatgctcc   20280
tgtcgcttgt gctcatggcc cttggcacat tgagcccgca gatggcatgg aatcaggtgc   20340
```

```
ctgttgcctt ggtgatggtc ctggcgacgg tgtcggtgac ggtggcggtt gaaatccctc    20400
tcattctcgc cttccgtgac cgtgccgcgg tgatgcgcat cgtggcgatg gccgtcatct    20460
ttacgatatg cgtactcgtc gttccgtca caaacaatca ggacatcctt gtcgccctga     20520
cctccattcc ggacgcctg ctgatgctga ttggcggtgt tgtctgcttg gtgtgcacgg     20580
ccgcatcagg gtcgatatcc catcgcctac tcagcagagc cgaatggtga ttgtcggaga    20640
ctgtggttgt gatgcagaca ccatcatgca cacaggggca tgaggggctt atcatggcat    20700
ggggcatgcc tgggaggcgg cttgggtatg ctcggcacca ctgtgacgct ctacaatact    20760
ctcgacgaac tcggcatcga ctacaccgaa gtcacacacc ccgcggttac gacaatggag    20820
gccgcacaat tcgtcagaac gctcatcgac ggcaccccga tcaagaatct attcctcacc    20880
aatcgaaaag gaaactacta tctcgtgctg atgagcgagg atcggcgagc ggatctcaag    20940
gctctcgcac agatcatcgg tacgggccgg ctctcatttg cgaatgccga cgatctgcgg    21000
cgcgtattga acctcgaacc cggatcggtg actccgctcg cactcatcaa cgatgccgac    21060
caacaggtcg aggtgctggt cgatactgcg ctcgcaggac agcgtctgct catgcatccg    21120
aatacgaaca cgaaggcgat gagtcccgaa tacggggatc tgctcaggtt cattgggcac    21180
acgggccacg gttacaggtt catctaagcc gcgcaattct tcggagctgc caggtatgcg    21240
gattacgacc gggttggcat ccacgcacct cgatgctgaa atggattcgt aatcgtcatg    21300
tcacagagaa tgttcctctc ttggctatcg tgctcatgtc catgtctgca tgacgatgag    21360
ggaacggagg gcatatgagg ccagtagtcg cggtgatgcc gttggtggat gacgaacggg    21420
agagcctatg gatgcttccc gggtacatga atgcattgcg tgaggccggt gcagtgccgt    21480
tcatgcctgc attgacgacc gatcgacagg agatcgggca gatcttcggc atgtgcgacg    21540
gccttgtgat gactggtggg catgacgtga atccggcatg ctacggtgaa tcggaccgat    21600
acggcaatct gcactgctgc gatgcgcggg atgagatgga actcgcgttg cttgaacgtg    21660
ccgttgcaag cgacaaaccg gtgctcggca tatgccgtgg tctgcagatc atgaacatct    21720
tctgcggagg gacgctgtat caggatctgc cgagcgaaca tcccagcgac gtcgatcatc    21780
atcagcaccc accctatggt cggccggccc accatgtgca cattctaagc aggacgcccc    21840
tgcgagaaga tttacacgac accgaccttg cggtcaacag ccggcatcat caggccatct    21900
gcaagctggg cgaggggttg gatccgatgg cgatcagcga ggatggtctc gtggaagcga    21960
tctacaggcc tcgaagtgca ttctatcgtg ctgtgcaatg gcatcctgaa catctatata    22020
aagtagacga accaaacagg tgcatattcc gctccttcgt gaacgcctgc acactccgag    22080
attgaatgtg gcagtgcgcg ggccaatcca atatgccaca agctacgggc gtattggatg    22140
taaatgtcgt tagcatggag gcaacaggac acggcaactg acgacaccta cggacgcgaa    22200
cggatatggc gatagacaaa ccaaaccatg agaccatgtt gcaatgcttc gaatggtacc    22260
tgcccgaaag ccacaaccta tggagatggc tctcatcgca ggcgccgagc gtggcccatg    22320
ccggattcac cacagcttgg cttccacctg cgtacaaggg gcaggccggc gattcagacg    22380
tgggatatgg cgtctatgac atgtacgatc ttggagagtt cgatgccaaa ggctctgttc    22440
ccaccaaata cggctcccgc atggagtacc ttcaggcgat tcgcgcgatg cagggcaatg    22500
gtgttcgtgt attcgcggac atcgtgttca accaccgcat gggtgccgat ggaacggaac    22560
ccgtgcgcac acatgaagtg aatgtggacg accgcacgag aagcgactcc accgtggtcg    22620
aacgcacctt gaacaccgta tacgatttcc ccgaacgcgg cggcgtgtat tcgacattca    22680 aatgaactg gagcgatttc accggcaccg attacacgac cgatgatggc acgacgggca    22740
```

```
tcatgcgttt cgacggcaag cagtggagcg acaatgtgag ccatgaacgc ggcaacttcg    22800
attacatcat gggagatgac gtcgatgtca acgaacctga ggtcgccaga gagcttacgg    22860
attggggcat atggtatacg acgaccacag gagtggacgg cttccggctc gatgcggtga    22920
aaagcatcga cgccggattc ttcgcgccat ggttgcgcac gatgcaacga tacggcaatc    22980
atcccggcat tgccgtgggt gagtactggt cgggtgacgc gagcgagctg acctcgtacc    23040
tgcatgattg caaccattgc atgatgctgt tcgatgtcgc gctccatttc cgcttcgaac    23100
aggcctcaaa gaacccagag ggattcgatc tgcgggact tgccgcagac acgctgtatg     23160
agcgtgaacc gacgtatgca tgcaccttcg tggacaacca tgacacacaa cccggtcagg    23220
cgctcgaatc ctgggtgcaa ccatggttca aaccgttggc gtacgcatgc attctgctac    23280
gcgacaacgt gttgccttgc gtgttcttcg gcgattacta cggcgtaccc cacgatctca    23340
tcccgccaat gaggttcctg ccgcacatgg tgtggatccg cgcgcatctg ctgggggatc    23400
aggtggaggc gcagccaggc gataccgccc attcgctgtg ctgggtggtg aaggaaatc     23460 acccggtgtg cgtggtgctc aacaccggga gcagcgaggt ccatcgacag gttcgcaatg    23520
cggcgctcgc ctcgcacacg cttatcgacg tatgccatcc tgatgccccg gcgacgactg    23580
acacgcaggg gcagggcatg atgcgatgcc ctccgcggtc atgcgccatc tatattgatg    23640
cggacgatta tggggtgatg ttggaagcgt tgtccggcac gcccgcagct gggactgtat    23700
gcgcctgaga gcataggtgc gccacaagcg gagtctatgc ctctagacta agaataaccg    23760
gccagctatg cgctaatgtc tgtagaggtt gacaccgggg aggagaggga gacaatgacg    23820
aagcaacaca agggcggtgc agattcacca gtgtctcccg atacgcagaa tccaggaagc    23880
ggaaccaggg cacaggatgg tttggcagca cacgcccaca atgcggcaat acgcgcacaa    23940
gtccaccgga tgcaggcgat agccgaggag gatgaccgct tcggctatga caggcatgcg    24000
accaaccggg ccctgagcat cgcaaatggt gtgaccgtca tcattctcgg attcgccctt    24060
ggaagcttcc tgcaggcatt gccggaacgc aacaccgccg acgtgcagga ggtggtcaaa    24120
gggctcgatc ggctgattgg cctcatgacc aaggaattgg tggagctgcc gcatatccag    24180
cggcatccgg aatcgttcat tgcggaaatc gttggaatcc tgatcggtta cacgattctc    24240
aagcatgcgc atgaggacag ccgggaatac gacgccgcat tcaatcggat cgagcagttc    24300
tacacagtgt cgcagaggcg ccgggggtgg attcgctgcg ggggttctggt ggttctgggc    24360 accgtggtga ttctcgtcac ccatggcctg ctgctggctt acggtcatgg catgggtgac    24420
ggcatcgccg ccggcattgc gcagaccagc atcgcggcgg gggtgtggtg ttatgtgtat    24480
gggggtctgt acgcaacgcg caccgatctg ttcctctata atttccgtgc gttgcgccaa    24540
gtcaacgtct acgagctggg gaaaagcgaa agcgatgcgc gccgtgagat gagactcgga    24600
gagaagaggc tatgcgactt atcgtcgtcg ctcaccaact tcaccgtggc catcggtgtg    24660
ctcggagcgc tggggctta cttcctgccc accttccgtt cacagtactt ctggcttcca     24720
ctcgttgtga tgatcggcat cgctttgtgc atgcggtggt tcgtgatccg ctatgcgcgg    24780
cggcggtacg aacctgattt cgattagttt cccatatacg ccgcggcgcc ggcgagcagg    24840
cgcgccgtgc cgccgatgac cagatcggcg cgggtgccga gattcatgcg tacgaaccgg    24900
gatccgtttt cgccatagat gccgccatac gagagcacaa gaccggtatg tgagcgcaga    24960
aaaccgcaga agcgctcagc attggcgtca cccacacgat caagaaggcc cgagcagtcg    25020
atccatgcca gatacgtgga atccgaggcc accatatgca gcatgtcatg tgcatgctcg    25080
tcaagttgcg tcgacacgta gtccttgttg cgctgcagga cacggcacag atcgtcgagc    25140
```

```
catgcgcctc catctgcata ggcggcgatt gtggagaaca cggcgaaatc gttcggcccg    25200
gccacctcgt cggtgttcac gccgcgcacg gcacgtgccc ggagaccgtc atcgtcgcag    25260
atgaaatatg cggactgcag tccggccaca ttgaaggcct tcgatggcga cgagcaggtc    25320
acgcagattg aacggttcag ctcgttgacc gcggcgaatg gcatatgggt gacgcccggg    25380
cgcacgatgt cgccatgcac ctcatcggga acaaccgtca catggtgctt tgcacacagt    25440 tccctacgc gcgccagatc gctgtcgctc cacacgttgc cactcggatt ctgcggattg     25500
cgcagaatca tcagacgggt gagcggatcg gcgagcttgc gtccgagatc ttcgaaatcc    25560
atcgagcaca caccatgctc gtatcgcagc ggattgttca gtacgacg tacgttgttc      25620 actagcgaat tcgtgaagat gttatagacc ggcggttgga gcacgacctt ctcagccaca    25680
ttcgtcagcg agcgcaccag cgaggagatc gccggaatca caccggtggt gaacaccaca    25740
tgctcagaat ccaccgtcac gccatactgg cgtagcgacc aatccgcgac cgcttcggtc    25800
cattcccggg gaacatccgc cgaaggtgcc gttgcccacg cgttcagcca atgcctcgct    25860
gatcgccgga gccgtgcgga aatccatgtc cgccacccac atcggcaact ccccatcggc    25920
cacgtcccat ttcatcgaga agatgcccgt gcggtcgaca ggggagtcga attgtgcaat    25980
gcgctcgtca atgtccatgt tgtgcctcgc tgctccgtga atcataggtc tgtgctgatg    26040
agctggatct tcgtcgtgtc tatcgcgggg tcgttctgca ggacgtcgcc gaatgcggca    26100
gcgcgaatca cgccggaaat cgggttgacc acgctgtcga tgcgtgtggt gacgtcggcg    26160
tcgatgtcgg aacagtattc gaacgagcgc gtcgtgttga tcagacggca gtctcgcatc    26220
gtcagcccgt caatgtagca cagtccctgc agcgattcga tggtgcagtt ctcgaatgtg    26280
atgttcttcg tgttccatgc caaatactcc ccgctgatga acgagttgcg caccgtgaca    26340
ttctcgcagt tccagaaggc atccttcgaa atcagacggg catgatccac cgtcacgttc    26400
cgtgcgccgt cgaaacagta attgccggtg agctgaaaat cgcgtatgtc cagattctca    26460
ctgttcatgg caaagtagtc gccggcggcg ctcacttcgc gcaatgtgac cttcctgcat    26520
tcccagaagg tctccgcggc atcagtgaat gcggtgcgct ccacggtcac atgctcattg    26580
cgacggaatt ccttgggtgc ctggatggtg cagtcgtgga acgtcatgtt cttcgagtac    26640
cagaacgccg cgtgggcatt gaattcgaac agactgtgct ccacctcgac gccctcgctg    26700
taccacagcg gatacttcca gcggaacacc gaatccctga ccacgatgtt gcgtgattcc    26760
ttgagcggcg actcgccgtc ctcgaacacg caatccgtga tctgaagatc acgaccttgg    26820
aacagtgcgc gttcaccact gagcagctgt tgcgtaatcg cttgcatagc atcttttcag    26880
actcgtgtat ctcatacaat acgcgtgcgg cacttgc                            26917
```

<210> SEQ ID NO 2
<211> LENGTH: 30
<212> TYPE: DNA
<213> ORGANISM: Artificial sequence
<220> FEATURE:
<223> OTHER INFORMATION: Synthesized: Primer mdy100

<400> SEQUENCE: 2
cgcaccgggc cccctcacgc aaactctacg                                        30

<210> SEQ ID NO 3
<211> LENGTH: 33
<212> TYPE: DNA
<213> ORGANISM: Artificial sequence
<220> FEATURE:
<223> OTHER INFORMATION: Synthesized: Primer mdy98

```
<400> SEQUENCE: 3
tgtggtgtat cacatgtgat tgtcctccct tta                                33

<210> SEQ ID NO 4
<211> LENGTH: 32
<212> TYPE: DNA
<213> ORGANISM: Artificial sequence
<220> FEATURE:
<223> OTHER INFORMATION: Synthesized: Primer mdy99

<400> SEQUENCE: 4
aggacaatca catgtgatac accacagcga gg                                 32

<210> SEQ ID NO 5
<211> LENGTH: 32
<212> TYPE: DNA
<213> ORGANISM: Artificial sequence
<220> FEATURE:
<223> OTHER INFORMATION: Synthesized: Primer mdy89

<400> SEQUENCE: 5
ccgtccaagc tttctatcgc gagataatca gc                                 32

<210> SEQ ID NO 6
<211> LENGTH: 10267
<212> TYPE: DNA
<213> ORGANISM: Artificial sequence
<220> FEATURE:
<223> OTHER INFORMATION: Synthesized: Plasmid pMDY28

<400> SEQUENCE: 6
ctaaattgta agcgttaata ttttgttaaa attcgcgtta aatttttgtt aaatcagctc    60 atttttaac caataggccg aaatcggcaa atcccttat aaatcaaaag aatagaccga    120 gataggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt ttttgggt cgaggtgccg taaagcacta atcggaacc ctaaagggag     300 cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta tagggcgaat tgggtaccgg   660
gccccctcac gcaaactcta cggcgtgcag tggcatcctg aggtcaagca cacgccgttg   720
ggacaggatc tgatcgagaa tttcctgcat gattgcgccg gcatcgaagc cgattggaac   780
gcaaggaaca tcatcgacga gcaggtcgct gcgattcgtg agaaggtcgg tgacgcacgg   840
gtcatctgtg gtctgtctgg tggagtcgat tcggccgtgg ctgcagcgct cgtgcaccgc   900
gcgatcggtg accagctcac ctgcgtgttc gtggatcacg gtctgctacg caagggcgag   960
gccgagcagg tcaaacatga tttcgtcgcg gcgaccggca tcaagctcat cgccgtcgat  1020
gcctccaagg atttcctcga tgcactcaag ggcgtctccg atcctgagac gaagcgcaag  1080
atcatcggcg aaaaattcat ccgcactttc gagaaggcgc agcgccaggt gatagaggag  1140
gccggtgccc agggcaagga ggtcaagttc tccgtgcagg gcacgcttta cccgacgtc   1200 gtcgaatccg gtggcggcga cggcgcctcg aacatcaagt cgcatcataa cgtcggtggt  1260
```

```
ttgcctgacg acatcaagtt cgaactgatt gagccgctcc gttcgctgtt caaagacgag    1320
gtgcgcgcca tcggcaccga actcggcttg ccggacgaga ttgtctggcg tcaaccgttc    1380
cccgggccgg gtctgggcat ccgcatcatc ggtgagatca cgaaggaacg tctcgacttg    1440
ctgcgtgatg ccgatgcgat tgcccgcgag gagctctcga aggccggtct cgaccgcgac    1500
atctggcagt gcccggtcgt gctgctcgcc gacgtgcact ccgtcggcgt gcagggcgac    1560
gaacgcacct acggttcgcc gatcgtgctg cggccggtca gctctgagga cgcgatgact    1620
gccgactggt cgcgtgtgcc gtacgacgtg ctcgccacca tctcgactcg catcacgaac    1680
gaatgccgtc agatcaaccg cgttgtgctc gactgcacgt cgaagccacc ggcgacaatc    1740
gagtgggaat aactgacaaa acccgcaaag ccttgaaaac actgggtct taaagcggaa     1800 acggggcatt tgatagcaaa ttgatagcag ataccaaaac cggatttact ttgttcactc    1860
ccgtataacg ggtggcttgc gggtaaatcc tccatatcct aagaaaaagg tcttgctgac    1920
tttcaccagt cggcaagacc tttttgtta tttgtctttt ctctgtttct tcaatccttt     1980
tatcagagca tcgcttaatt ccttcgaggg gactttggcc caccgctggg tggtgtcgta    2040
cttcgggtag ttgtagcgcc agcggtcata gtcctccttg gtgatctccc cggcctccaa    2100
cttcgccgcc tgttcccgcc acgcaatcaa gattttgttc agctcactgg cttgacggcc    2160
tccctgaaaa atatctgctt gcaggcaggc acgtccatcc gcctctacca ctttcagact    2220
gtaaacatcc tccaaggcga acagcgtatg ggccaaacct atgtagttgt ctatgtccgg    2280
gacgctcaac gcctggggcg atacatctaa ggcaataccg cacagaaaaa aagtgccata    2340
tatcgccaag tgtgatataa caaacttatg gataaacaga tgacgatttc cgcattcagc    2400
gacgaactgg cacaggtgcg gacgaagaaa aaagcatttc tcgaccagat tgaacggatc    2460
gtcccgtgga aggaatggct tgccatgatt cagccgtgct attacaaagg agagcgcggc    2520
aacaaaccct atccgctgga gatcatgctc cgactgtatc tgctgcaaaa cctctatgac    2580
ctgagtgacg aggccacggt ggcagaagcc atcgacagcc gcgcattttc ggagttctgc    2640
ggcgtcgatt ccagcaacca ggttccgaac ggggatactc ttggccggtt ccggaacttg    2700
ctgatcaaga acgactgca ggagaagctg ttcgctcagg tggtagcagc gctcatggaa     2760
cgtggcctca ttctgaaaaa gggcaccatt gtagattcca ccatcatttc cgcccctct    2820 tctaccaaga ataaggaaaa gaaacgggat ccggatgccc accaagtcaa gaagggcaac    2880
acctggcact tgggtacaa agcgcatatc ggcgtggaca aggacagcgg actggttcac     2940
acagtggaag ctacaccggc aaatgtccac gacgttgcgg aagtgccgaa attattgacg    3000
ggagaggaag aaacagtcta tggagacagc ggttatctcg gcgcaggtaa gcgcgaagat    3060
gccgtagtcc gaaacaaagc tggccggaaa atcaagtaca agatcaatcg tcgtccatcg    3120
cagatgaaga aactgagcaa aagcgggcag tacgcagcaa agaaagcgga acgggcgaaa    3180
tcctcagtgc gagcaaaagt agagcatgta ttccgtgtcg ttaagaagca gctgcgcttc    3240
cgaaaaacgc gataccgagg gcttgaaaag caacaagcca aattcaatat catgtttgcg    3300
ttggcaaatc tgattctggc tgacagaccc tgtctggcag cttgagtcag tgcgcctttg    3360
cggacaaaaa attcggaggt tatccacagt ttttattcgg cacctgctgt ataatgcgga    3420
ttgtggcatt tgtgcggtgt tgccttaaat aaaactataa tcaaatagtg gaacaaagg    3480 attatgatag tcccttttgt aggggcttag ttttttgtac ccaatttaag aatacttttg    3540
ccttatcaat tttgacatat ccccaaaaac agcactcaca aacaggtgta tgctgtatat    3600
gtgtatgtcc gcaaattatc atcccagtg gtaaaagtat tttactgctg gggattttta    3660
```

```
tgcccttcgg ggcagtaaag ggaggacaat cacatgtgat acaccacagc gaggaaggtt      3720
attgcatttc cctgtctttc gtggtaaaat gtagttgtaa accaccagag aaaccaatct      3780
aattttaccg ttgatagcca tttccttgat agccaaatga tagcaaaagt tcggcaagcc      3840
cataggataa ggataatagg tatcaggaaa aatcaaatga tatcaaatct cccaaacaaa      3900
agcgtttaga attaagtttc attttgcgaa tgggagtgac cccgccgatc atgcgaccat      3960
cgctcccata gcgtctttct ttgcaggtgg cgcccgccga agcctatctt cggcgggcgc      4020
cacctgtcgt cgttctgcta tccagtatcc agtttcttct catggaaggt gccccggacg      4080
acgattacga cgtggacatc gatttggatg cgggcttcaa ggtgggacgc catgacgtcg      4140
aatccatccg aagacccgaa ccgggacgcc tcccaagggg aggggggaat gcgatccgta      4200
tccgctagaa gcgcgcccgc agtcgatagg gcaaatcatg aacatgtgac cggcaccgga      4260
aagtgacata atccgattgt cggcaatggg ctcgatatgg tatcagccga gcagccagtc      4320
gacgatattg cgtatctcaa tgccgtcaga ggtcgtgccg agacggaatc tgtcgagtgt      4380
gagcacgatt ttcgggaatg catccgataa cgattgcaaa ggcgcgagtt ccctcgcgcg      4440
ggtggattct tcgagcatcg tcccggtgac ctgaatgtag attctcctgt cgaatcgttg      4500
agcgacgaaa tcgatttcac ctccacgcag actgccgaca tgcacgttgt acccgcgtct      4560
gcgcagctcg ttcgcgacga cgttctccaa ttggaatccg tagttttgtg aggagaaacc      4620
atttgcgatg ttgcatagtc cggggtcttc ggcgtggaac ttgcgatgtg tcacaaaccg      4680
ctgaaggtgt caggtataac tgacatttct cggatttcaa gatggtttgt cgggtataac      4740
tgacggatct gtttgagggt gcatcccgta agaaagtgca gccggtaagt ggatatagag      4800
gatatggggt atacggttgc aggaagcgag tgaatgggt gtgatgatcg acaaccatgg       4860
atgcggttac gggatacagt ggtatgcgcc gtgtgcttgt catcggatgt ccgggtgcag      4920
gcaaaagcac gttcgcgcgc aggttgcggg atgcggccgg actgccgctg cattatctgg      4980
acatgctgtg gcacaatccg gaccggacga ctgtcacacg ggccgaattc gatgagcggt      5040
tgcaaaggat cctcgaggag gatgcctgga tcctcgacgg caatttcgcg cggacgctgc      5100
cgaaacgact ggaatattgc gacaccgtgt tcttcctcga cttcccgacc gacgtatgtc      5160
ttgagggcgt cgagggatgt agcggtatga agcgcgaaga catgccgtgg gtcgaacacg      5220
aattcgatga ggagttccgt cagtacatca tcgactttcc cgctgagcgg cgtccgcaga      5280
tggttgacgc gcttgaagac gccgccgcgc gccgcggtgt gcgtgtccat accacatcca      5340
aggcagagct ggtgcaagcg ctcgctgatg ttttgagtgg tcttgaagtg gggcgggcca      5400
gagcatgtct gacgttcatc atgtaccgtt atgcgacata ctgggcatca cggtgaacga      5460
actgcttggt ggggggaggaa cttacaaaag tggattcccg tcagctccat cctccgtcgt      5520
ctcatcgtat gcgagcgcga gggcaccatc gtctcctcat gtgtatgcgt catcatcccg      5580
aatctgacgc ggggtgtgcg gccatacgcg ttcgtcgaga acgtcgtgac gcgcgccgat      5640
gcgcgtgggc atggttatgc taccgcatgt ctgaaccatg cgaaggcgct cgcgcagcag      5700
gccggctgct acaagatgat gctgctcacc ggctcccatg atccgaagac actcgatttc      5760
taccgccacg ccggctacag cagcaccgac aagaccgcgt tcatccagtg gctgtagggc      5820
gcgtccgtgt cacggtatcg catccaccac cgtcgatatc cgtttggcat cgctcgacgg      5880
cgggatgatg tggctgtcaa ccggaagtga acgtaggatg cgcagctccc gctctctgcg      5940
ctcttcaagg cacgcgatat accccctcata tccgcgcaac ccatgcgctt caccgtaccc      6000
ttgtgctgtg tggtagtcga tgacggcatt gagccaacca tcaccgcgtt cgtcgaggac      6060
```

```
accgtcaatc gccgatttcg cgcccggttc gtcaatgtag atgacgacgg gatgcagtgg    6120
cgcgatgatc gccgcaatat cgctgatgta ccgtcgtgac tcgtcctcgc tcatgccgaa    6180
ccgcatcatc gtctcgcaca tcggattctg cagcaggacg caattgaata cataggtcgt    6240
atcaggttcg gcgtgggctg cgaacgcgcg ccaagtatcg agtatcgtgg cgcgttcact    6300
tgcgaaatca gggaagtcgt ggtcgccgac atcggcggga tggtctgcgg ctccttcttc    6360
gacgcagacg acgttccttc cgcgcgcttc caattcggcg gcaaccatcg cagccgtcgt    6420
gcttttcccg ctatctggca gcccttcgac gatgatcaga cggggttcgca tctcatatgt    6480 gctcatgatg tcatggtacg gcgaaggata tgtgggatgt gcagatgtcc atgtatatag    6540
ggtgatataa ccgaatataa ggtgatatat agtgatatat cgaaatgaaa cgatatacaa    6600
ctcgctcggg agcatgttgt cgtcttttat gaattcatga tagatctgga ggaatcgttg    6660
ttttgagtcc atggatggtc gatgcgctca agcgcatgtg ctggtgcgcg tcgaacatat    6720
gaggccggtg aatgatatgc cgtatgccgc ttcttacgcc tcagcgggtg tcggtgatgg    6780
atggtcatgg aactcccgca tctccatatt gatgaatctg ctgattatct cgcgatagaa    6840
agcttgatat cgaattcctg cagccccgat tttcgttcgt gaatacatgt tataataact    6900
ataactaata acgtaacgtg actggcaaga gatattttta aaacaatgaa taggtttaca    6960
cttactttag ttttatggaa atgaaagatc atatcatata taatctagaa taaaattaac    7020
taaaataatt attatctaga taaaaaattt agaagccaat gaaatctata aataaactaa    7080 attaagtttta tttaattaac aactatggat ataaaatagg tactaatcaa aatagtgagg    7140
aggatatatt tgaatacata cgaacaaatt aataaagtga aaaaaatact tcggaaacat    7200
ttaaaaaata accttattgg tacttacatg ttttggatcag gagttgagag tggactaaaa    7260
ccaaatagtg atcttgactt tttagtcgtc gtatctgaac cattgacaga tcaaagtaaa    7320
gaaatactta tacaaaaaat tagacctatt tcaaaaaaaa taggagataa aagcaactta    7380
cgatatattg aattaacaat tattattcag caagaaatgg taccgtggaa tcatcctccc    7440
aaacaagaat ttatttatgg agaatggtta caagagcttt atgaacaagg atacattcct    7500
cagaaggaat taaattcaga tttaaccata atgctttacc aagcaaaacg aaaaaataaa    7560
agaatatacg gaaattatga cttagaggaa ttactacctg atattccatt ttctgatgtg    7620
agaagagcca ttatggattc gtcagaggaa ttaatagata attatcagga tgatgaaacc    7680
aactctatat taactttatg ccgtatgatt ttaactatgg acacgggtaa aatcatacca    7740
aaagatattg cggaaaatgc agtggctgaa tcttctccat tagaacatag ggagagaatt    7800
ttgttagcag ttcgtagtta tcttggagag aatattgaat ggactaatga aaatgtaaat    7860
ttaactataa actatttaaa taacagatta aaaaaattat aaaaaaattg aaaaaatggt    7920
ggaaacactt ttttcaattt ttttgtttta ttatttaata tttgggaaat attcattcta    7980
attggtaatc agattttaga aaacaataaa cccttgctat gggggatcc actagttcta    8040 gagcggccgc caccgcggtg gagctccagc ttttgttccc tttagtgagg gttaattgcg    8100
cgcttggcgt aatcatggtc atagctgttt cctgtgtgaa attgttatcc gctcacaatt    8160
ccacacaaca tacgagccgg aagcataaag tgtaaagcct ggggtgccta atgagtgagc    8220
taactcacat taattgcgtt gcgctcactg cccgctttcc agtcgggaaa cctgtcgtgc    8280
cagctgcatt aatgaatcgg ccaacgcgcg gggagaggcg gtttgcgtat tgggcgctct    8340
tccgcttcct cgctcactga ctcgctgcgc tcggtcgttc ggctgcggcg agcggtatca    8400
gctcactcaa aggcggtaat acggttatcc acagaatcag gggataacgc aggaaagaac    8460
```

-continued

| | |
|---|---|
| atgtgagcaa aaggccagca aaaggccagg aaccgtaaaa aggccgcgtt gctggcgttt | 8520 |
| ttccataggc tccgcccccc tgacgagcat cacaaaaatc gacgctcaag tcagaggtgg | 8580 |
| cgaaacccga caggactata aagataccag gcgtttcccc ctggaagctc cctcgtgcgc | 8640 |
| tctcctgttc cgaccctgcc gcttaccgga tacctgtccg cctttctccc ttcgggaagc | 8700 |
| gtggcgcttt ctcatagctc acgctgtagg tatctcagtt cggtgtaggt cgttcgctcc | 8760 |
| aagctgggct gtgtgcacga accccccgtt cagcccgacc gctgcgcctt atccggtaac | 8820 |
| tatcgtcttg agtccaaccc ggtaagacac gacttatcgc cactggcagc agccactggt | 8880 |
| aacaggatta gcagagcgag gtatgtaggc ggtgctacag agttcttgaa gtggtggcct | 8940 |
| aactacggct acactagaag gacagtattt ggtatctgcg ctctgctgaa gccagttacc | 9000 |
| ttcggaaaaa gagttggtag ctcttgatcc ggcaaacaaa ccaccgctgg tagcggtggt | 9060 |
| ttttttgttt gcaagcagca gattacgcgc agaaaaaaag gatctcaaga agatcctttg | 9120 |
| atcttttcta cggggtctga cgctcagtgg aacgaaaact cacgttaagg gattttggtc | 9180 |
| atgagattat caaaaaggat cttcacctag atccttttaa attaaaaatg aagttttaaa | 9240 |
| tcaatctaaa gtatatatga gtaaacttgg tctgacagtt accaatgctt aatcagtgag | 9300 |
| gcacctatct cagcgatctg tctatttcgt tcatccatag ttgcctgact ccccgtcgtg | 9360 |
| tagataacta cgatacggga gggcttacca tctggcccca gtgctgcaat gataccgcga | 9420 |
| gacccacgct caccggctcc agatttatca gcaataaacc agccagccgg aagggccgag | 9480 |
| cgcagaagtg gtcctgcaac tttatccgcc tccatccagt ctattaattg ttgccgggaa | 9540 |
| gctagagtaa gtagttcgcc agttaatagt ttgcgcaacg ttgttgccat tgctacaggc | 9600 |
| atcgtggtgt cacgctcgtc gtttggtatg gcttcattca gctccggttc ccaacgatca | 9660 |
| aggcgagtta catgatcccc catgttgtgc aaaaaagcgg ttagctcctt cggtcctccg | 9720 |
| atcgttgtca gaagtaagtt ggccgcagtg ttatcactca tggttatggc agcactgcat | 9780 |
| aattctctta ctgtcatgcc atccgtaaga tgcttttctg tgactggtga gtactcaacc | 9840 |
| aagtcattct gagaatagtg tatgcggcga ccgagttgct cttgcccggc gtcaatacgg | 9900 |
| gataataccg cgccacatag cagaacttta aaagtgctca tcattggaaa acgttcttcg | 9960 |
| gggcgaaaac tctcaaggat cttaccgctg ttgagatcca gttcgatgta acccactcgt | 10020 |
| gcacccaact gatcttcagc atcttttact ttcaccagcg tttctgggtg agcaaaaaca | 10080 |
| ggaaggcaaa atgccgcaaa aaagggaata agggcgacac ggaaatgttg aatactcata | 10140 |
| ctcttccttt ttcaatatta ttgaagcatt tatcagggtt attgtctcat gagcggatac | 10200 |
| atatttgaat gtatttagaa aaataaacaa ataggggttc cgcgcacatt tccccgaaaa | 10260 |
| gtgccac | 10267 |

<210> SEQ ID NO 7
<211> LENGTH: 19
<212> TYPE: DNA
<213> ORGANISM: Artificial sequence
<220> FEATURE:
<223> OTHER INFORMATION: Synthesized: Primer mdy94

<400> SEQUENCE: 7
gagcatgtat tcggtgtcg                                              19

<210> SEQ ID NO 8
<211> LENGTH: 18
<212> TYPE: DNA
<213> ORGANISM: Artificial sequence
<220> FEATURE:

<223> OTHER INFORMATION: Synthesized: Primer mdy95

<400> SEQUENCE: 8
gatttgccct atcgactg                                                        18

<210> SEQ ID NO 9
<211> LENGTH: 34
<212> TYPE: DNA
<213> ORGANISM: Artificial sequence
<220> FEATURE:
<223> OTHER INFORMATION: Synthesized: Primer mdy82

<400> SEQUENCE: 9
cgacccaagc ttggatcggc tcgtgcatca ttgc                                      34

<210> SEQ ID NO 10
<211> LENGTH: 20
<212> TYPE: DNA
<213> ORGANISM: Artificial sequence
<220> FEATURE:
<223> OTHER INFORMATION: Synthesized: Primer mdy83

<400> SEQUENCE: 10
gcaaaccgta cctcaatacc                                                      20

<210> SEQ ID NO 11
<211> LENGTH: 32
<212> TYPE: DNA
<213> ORGANISM: Artificial sequence
<220> FEATURE:
<223> OTHER INFORMATION: Synthesized: Primer mdy84

<400> SEQUENCE: 11
cgacccaagc ttgcagtccg tcaattaggg tg                                        32

<210> SEQ ID NO 12
<211> LENGTH: 20
<212> TYPE: DNA
<213> ORGANISM: Artificial sequence
<220> FEATURE:
<223> OTHER INFORMATION: Synthesized: Primer mdy85

<400> SEQUENCE: 12
cgttgctgac gttgcggttc                                                      20

<210> SEQ ID NO 13
<211> LENGTH: 10504
<212> TYPE: DNA
<213> ORGANISM: Artificial sequence
<220> FEATURE:
<223> OTHER INFORMATION: Synthesized: Plasmid pMDY24

<400> SEQUENCE: 13
gaattcaaga cttggaccgc aaacgtcgtt catcccacac aatgggaggg cgaacggaac    60
acacagtcca atcaagagtt cgctcgccgc aacaccattg agcagttgca cgcgggcagg   120
tttgcaagaa gagggctcaa atatgactgc tgctgaacag cagatttccg gcaatcccgc   180
ggctatggaa aacgcacaag cacgtaccac cgtgacggat caagccaagg ttcaggatat   240
tatctcgcgc atggatcgcg cacatgaaac cccgatgttc catcgcatcg tgacgctggt   300
cgccgctggc atgctgatgg acagcatcga cgtatatatt ggcagcgccg tcgcctccag   360
cgcgttggct acccactggt ccaccgttgc gcaaaattcc acctttatgt ccgcaggctt   420
cctgggtctg ctggtcggtt cgctgctggc cggcttcgtc ggtgacctga agggccgccg   480

```
cgtggcttac caaatcaacc tgttgctgtt tggcggcttc accttcctcg gcgcattcgc    540
cccgaacatg gccgtgctgt ccctgtgccg tctgggtgcc ggcctgggcc tcggcgctga    600
aatcgtcacc ggcttcgcca tggtcaacga gttcgcaccg atgaaccgcc gtggccactg    660
gtgcgcgatt gtctcgctcg tggccaactg cggtgtgcca atcgctatgc tgctgtgcgc    720
atggatcatc ccccgctggt cctggcgtcc gctgttcgtg gccatcggtc tggggggccgc   780 catcatctgg tggctgcgcc gcgacatccc cgaatcccg cgttggctcg ccgtgcacgg     840
ccgttacgat gaggccgacg ccatcgtcaa gcagcttgag gccaacggct ccgaaccgat    900
cgacgcagcc gccaaggccg acaccagcga cacccgcaac gccggcggcc gttcgctcgg    960
catctgcctg cttgtggctg tggttgctgt ggccgccacg aacgtgtgct cctacgcctt   1020
cacttcttgg gttccgacga ttctggtcaa gcgtggtatt aacctgtcca gctcgctgct   1080
cacctccacg gcgatgatgc tcggcgcccc ggtcggctgc ctgattggct ctctgcttat   1140
cgaccgcatc ggccgcaagc gcacgattgt gccggccttc ctgttcactg gcgtgttcgg   1200
tttaatgtat gccttccaga cctctaccgt gagcgcaatt atcgttggct tcctgctcat   1260
gatgtgcctg tacgtgctta tggcttccgt ggtggctgtg tacgctccgg aactgttcgc   1320
caccaaggtt cgcttccgtt gcgtcggctt cgcgaacgcc gtggccaagc tgctcaatgt   1380
gttgatgccg atggtggtgg gctggatgct tacctcgctt ggtgtcacgt ccatctttgt   1440
ggccatcagc gcgattgcta ttgcatcgat gctgattgtc ggcttctttg gcgcggagac   1500
tgcgcagaag tcggttgggt gatcggtttc ctcacagtgg aataactgct gatgatgtcc   1560
attcggcgtc ttgcgtggtg atatgcaggg cgccgttttg ttgttctagt aattgtcggt   1620
aacggttgag gccggtgccg gtggataggt ctgcgtctcc agcggacaat cagcgtctgt   1680
gatgtcacat gcaatgccag gagcggcatc aacggtcgaa tcatgcggag tcactgcact   1740
gtgcgccgct tctcccctgc cttcaatcac atcaatgact tgatgcgtgc gatccaatgc   1800
gcccatagac atatccgtaa ccagcacgtc aggccgcttg gtggggctca ggcatcggct   1860
gatggccacg gcacccaaat cgcaggtcta tatcacggca aaatcgctgg acatacgttc   1920
gattagcgcg ccgaacactt tcagcgcata tgggtcattg tccacaatgc cgatgagtat   1980
gttgcggttg cgcgcttctc ccattacatt cacccctctca gtgtgcccga cgccgaactg   2040
ctccgtcctg acatgtcatg gtcactatga caactatcat tccacattc ctgcgtgatt    2100 tacgatggaa tcatcatcaa tccttgacaa ggcggtaaag gaggacggca atgaaccgtg   2160
cacaagcact cagcaagctc aacaggagcg atatgcgcaa tgccgccgcc gagcgcggga   2220
tgcaacgact gttcacatgg aaccgcgcgc attggattgg catggttgta ctgatagcgg   2280
tgttgctgct actgcagtgg agctcatcaa tgtatctcat gcccgacgag gttcttgaca   2340
gggctgccaa aaacctgttc gtatggttcc ccggtatggt tctgcactgg ccattggtgt   2400
tggaaatcac caacttgata ctcggttcga cacgatccgg cagtctgtct ttcccgttgg   2460
cgagcgcaat catcggacca ctggcattcg gctggaccaa tcttcgctta cggccggggt   2520
tcccataccg ttcctgggct caagggaaag ccgcaatata atgaaaacag cgatttcgtg   2580
caatgatgca cgagccgatc caagcttgca gtccgtcaat tagggtgtat cgtttgacgc   2640
atggttacga tgaaggaaat cgcgaacaag gcggggggttt ccgtctctac ggtatcgctg   2700
gtgctcaacg gacgcgacga ggggcgcgta aagtccaaaa ttgcggacaa tgtgcgcgcc   2760
atcgccacca agctcggcta ccagtcgaat ccgctggcca gttcgctgcg tacaggcagg   2820
acgcacatcc tcggtttcat cagtgaggag gtggccacca ccccgtacgc cggcggtatg   2880
```

```
attctgggcg cgcagaccgc tgcaagccag ttcggctata tgctcatcac cgtgagcacc    2940
gacggcgaga acagcgagag cgaggaaatc gccgcactca agcgatacgg caccgacggc    3000
tttctgtacg ccaagatgtc gaaccgcatc acccatgtgc cttcctcgct ggccaagacg    3060
ccactggtgt tggtggatgc caccgactcg cttggcaaaa tcccgagcgt ggaaccggac    3120
gagttccaaa tcggctacga cgccaccacc agattggtta aggccggatg cgcacgtatc    3180
gcctatgtgg gttgcttgga gccgctgatt gcgcaggacg atcgtttgga aggctatcag    3240
gcggcgctca gggacgccgg cctcgactat gacgatcatc tggtcgtcaa tgtgctcaac    3300
aacgggccgg cactgaccgc agtcagcgat ttgttcgatg ccgagcatcc ggacggattc    3360
ttctgcttca acgatgcccg cgcctggtat gtgtacgaat gcgccgcacg ccgaggactc    3420
acggtcggca aggacatctc cgtggtcggc gtggacaacc atcgcgtgtt cgccgaaacg    3480
ctggaaccga tgctcaccac tgtggaactg ccacatttcg agatgggcta ctgggccgtg    3540
gccaagctgg tgtcgattat cgaaggacgc tcgatggacg acgtctcatg ccagcgacc    3600 accgctcccc tgccgccgat tgacgcgccg attccggcga agatccactg cacgctgatc    3660
gaaaagacct cggtgaagta gccgagtccc acacgatttc tcaaggcctc cgtccagcac    3720
ggaggccttt ttgcgtgtcg aacaggtacg acacgccgat ttacgtcaat cgattgacgt    3780
aaatcgattg acgtcgcata ataattacta cataacaact tctacaaagg cacggccgcc    3840
cgagcagaag cgttacataa ccaataacca accaagtagt aatcaaagga tgattatggc    3900
aagtgcaacc aagtctgcat ggaagaatcc ttcctatctg cagagctctt tcggcatctt    3960
catgttcttc tgctcctggg gcatctggtg gtccttcttc cagcgctggc tcatctcagg    4020
cgttggattg accaatgctg aagtcggcac catctactcc atcaactcgc tggccaccct    4080
ggtcatcatg tttgtgtacg gcgtgattca ggatcagctc ggcatcaagc gcaagctcgt    4140
catcgtagtc tcggtaatcg ccgcctgcgt tgggcccattc gtccaattcg tttacgcccc    4200
gatgatcctc gccggtggca ccacccgctg gatcggcgca ctcatcggct ccatcgttct    4260
gtctgccggc ttcatgtccg gctgctccct gttcgaggcc gtcaccgaac gctactcccg    4320
taaattcggt ttcgaatatg ccagtcccg tgcttggggc tccttcggtt acgccatcgt    4380
ggcgctgtgc gccggcttcc tgttcaacat caacccgctg atcaacttct gggtcggctc    4440
cgcattcggc cctggcatgc tcctcgtgta cgccttctgg gtcccggccg agcagaagga    4500
agagctcaag aaggaaaccg acccgaacgc agccccacc aacccgtccc tcaaggaaat    4560
ggtcgccgtt ctcaagatgc cgaccctgtg ggtgctcatc gtcttcatgc tgctgaccaa    4620
caccttctac accgtgttcg atcagcagat gttcccgacc tactacgcca acctcttccc    4680
cactgaagaa atcggcaacg ccacctacgg caccctgaac ggtttccagg tcttccttga    4740
gtccgcaatg atgggcgtgg tcccgatcat catgaagaag atcggcgtgc gcaacgctct    4800
gctgctcggc gctaccgtga tgttcctgcg catcggcttg tgcggcgtgt tccacgaccc    4860
ggtcaccatc tccatcgtca agctgttcca ctccatcgaa gtgccgctgt tctgcctgcc    4920
ggcattccgc tacttcactc tgcacttcga caccaagctc tctgccacgc tgtacatggt    4980
gggcttccag atcgcttccc aagtgggtca ggtcatcttc tcgacccctc tgggtgcctt    5040
ccacgacaag atggctcaga ttctgccgaa caacgacatg ggatcccgcg tgaccttctg    5100
ggtcatctct gccatcgtgc tgtgcgcact gatttacggc ttcttcgtca tcaagcatga    5160
tgatcaggaa gtcggcggcg acccgttcta caccgacaag cagcttcgcc agatggaagc    5220
cgccaaggcc tgaaaggaca gccatgactg acttcactcc tgaaacccct gttctcaccc    5280
```

```
ccatccacga ccacgctgct gaactggcaa aagccgaagc cggcgtggct gagatggccg    5340
ccaatcgcaa caaccgctgg tacccgaagt atcacatcgc ctccaacggt ggctggatca    5400
acgacccgaa cggcctgtgc ttctacaagg gccgctggca cgtgttctac cagctgcacc    5460 cctacgcac ccagtggggt ccgatgcact ggggccacgt ctcctccacc gatatgctca    5520
actggaagcg cgagcccatc atgttcgcac cgtctctaga gcaggagaag gacggcgtgt    5580
tctccggttc tgccgtcatc gacgacaacg gagaccttcg cttctactac accgccacc    5640 gttgggccaa cggccacgac aacaccggcg gcgactggca agtgcagatg accgcgctgc    5700
cggacaatga cgagctcacc tccgccacca agcagggcat gatcatcgac tgcccgaccg    5760
acaaggtcga ccgatgccct tgagagcctt caacccagtc agctccttcc ggtgggcgcg    5820
gggcatgact atcgtcgccg cacttatgac tgtcttcttt atcatgcaac tcgtaggaca    5880
ggtgccggca gcgctctggg tcattttcgg cgaggaccgc tttcgctgga gcgcgacgat    5940
gatcggcctg tcgcttgcgg tattcggaat cttgcacgcc ctcgctcaag ccttcgtcac    6000
tggtcccgcc accaaacgtt tcggcgagaa gcaggccatt atcgccggca tggcggccga    6060
cgcgctgggc tacgtcttgc tggcgttcgc gacgcgaggc tggatggcct tccccattat    6120
gattcttctc gcttccggcg gcatcgggat gcccgcgttg caggccatgc tgtccaggca    6180
ggtagatgac gaccatcagg gacagcttca aggatcgctc gcggctctta ccagcctaac    6240
ttcgatcact ggaccgctga tcgtcacggc gatttatgcc gcctcggcga gcacatggaa    6300
cgggttggca tggattgtag gcgccgcgcct atccttgtc tgcctcccg cgttgcgtcg    6360 cggtgcatgg agcgggcca cctcgacctg aatggaagcc ggcggcacct cgctaacgga    6420
ttcaccactc caagaattgg agccaatcaa ttcttgcgga gaactgtgaa tgcgcaaacc    6480 aaccccttggc agaacatatc catcgcgtcc gccatctcca gcagccgcac gcggcgcatc    6540 tcggcagcg ttgggtcctg gccacgggtg cgcatgatcg tgctcctgtc gttgaggacc    6600
cggctaggct ggcggggttg ccttactggt tagcagaatg aatcaccgat acgcgagcga    6660
acgtgaagcg actgctgctg caaaacgtct gcgacctgag caacaacatg aatggtcttc    6720
ggtttccgtg tttcgtaaag tctggaaacg cggaagtcag cgccctgcac cattatgttc    6780
cggatctgca tcgcaggatg ctgctggcta ccctgtggaa cacctacatc tgtattaacg    6840
aagcgctggc attgaccctg agtgattttt ctctggtccc gccgcatcca taccgccagt    6900
tgtttaccct cacaacgttc cagtaaccgg gcatgttcat catcagtaac ccgtatcgtg    6960
agcatcctct ctcgtttcat cggtatcatt accccccatga acagaaattc ccccttacac    7020
ggaggcatca agtgaccaaa caggaaaaaa ccgcccttaa catggcccgc tttatcagaa    7080
gccagacatt aacgcttctg gagaaactca acgagctgga cgcggatgaa caggcagaca    7140
tctgtgaatc gcttcacgac cacgctgatg agctttaccg caggcaatag ttacccttat    7200
tatcaagata agaagaaaa ggattttccg ctacgctcaa atcctttaaa aaacacaaa    7260 agaccacatt ttttaatgtg gtctttattc ttcaactaaa gcacccatta gttcaacaaa    7320
cgaaaattgg ataaagtggg atattttaa aatatatatt tatgttacag taatattgac    7380
ttttaaaaaa ggattgattc taatgaagaa agcagacaag taagcctcct aaattcactt    7440
tagataaaaa tttaggaggc atatcaaatg aactttaata aaattgattt agacaattgg    7500
aagagaaaag agatatttaa tcattatttg aaccaacaaa cgacttttag tataaccaca    7560
gaaattgata ttagtgtttt ataccgaaac ataaaacaag aaggatataa attttaccct    7620
gcatttattt tcttagtgac aagggtgata aactcaaata cagcttttag aactggttac    7680
```

```
aatagcgacg gagagttagg ttattgggat aagttagagc cactttatac aattttttgat    7740 ggtgtatcta aaacattctc tggtatttgg actcctgtaa agaatgactt caaagagttt    7800
tatgatttat acctttctga tgtagagaaa tataatggtt cggggaaatt gtttcccaaa    7860
acacctatac ctgaaaatgc ttttttctctt tctattattc catggacttc atttactggg    7920
tttaacttaa atatcaataa taatagtaat taccttctac ccattattac agcaggaaaa    7980
ttcattaata aaggtaattc aatatatttta ccgctatctt tacaggtaca tcattctgtt    8040
tgtgatggtt atcatgcagg attgtttatg aactctattc aggaattgtc agataggcct    8100
aatgactggc ttttataata tgagataatg ccgactgtac tttttacagt cggttttcta    8160
atgtcactaa cctgccccgt tagttgaaga aggttttat attacagctc cactgcctcg    8220
cgcgtttcgg tgatgacggt gaaaacctct gacacatgca gctcccggag acggtcacag    8280
cttgtctgta agcggatgcc gggagcagac aagcccgtca gggcgcgtca gcgggtgttg    8340
gcgggtgtcg gggcgcagcc atgacccagt cacgtagcga tagcgagtg tatactggct    8400 taactatgcg gcatcagagc agattgtact gagagtgcac catatgcggt gtgaaatacc    8460
gcacagatgc gtaaggagaa aataccgcat caggcgctct tccgcttcct cgctcactga    8520
ctcgctgcgc tcggtcgttc ggctgcggcg agcggtatca gctcactcaa aggcggtaat    8580
acggttatcc acagaatcag gggataacgc aggaaagaac atgtgagcaa aaggccagca    8640
aaaggccagg aaccgtaaaa aggccgcgtt gctggcgttt ttccataggc tccgcccccc    8700
tgacgagcat cacaaaaatc gacgctcaag tcagaggtgg cgaaacccga caggactata    8760
aagataccag gcgtttcccc ctggaagctc cctcgtgcgc tctcctgttc cgaccctgcc    8820
gcttaccgga tacctgtccg cctttctccc ttcgggaagc gtggcgcttt ctcatagctc    8880
acgctgtagg tatctcagtt cggtgtaggt cgttcgctcc aagctgggct gtgtgcacga    8940
accccccgtt cagcccgacc gctgcgcctt atccggtaac tatcgtcttg agtccaaccc    9000
ggtaagacac gacttatcgc cactggcagc agccactggt aacaggatta gcagagcgag    9060
gtatgtaggc ggtgctacag agttcttgaa gtggtggcct aactacggct acactagaag    9120
gacagtattt ggtatctgcg ctctgctgaa gccagttacc ttcggaaaaa gagttggtag    9180
ctcttgatcc ggcaaacaaa ccaccgctgg tagcggtggt ttttttgttt gcaagcagca    9240
gattacgcgc agaaaaaaag gatctcaaga agatcctttg atcttttcta cggggtctga    9300
cgctcagtgg aacgaaaact cacgttaagg gattttggtc atgagattat caaaaaggat    9360
cttcacctag atccttttaa attaaaaatg aagttttaaa tcaatctaaa gtatatatga    9420
gtaaacttgg tctgacagtt accaatgctt aatcagtgag gcacctatct cagcgatctg    9480
tctatttcgt tcatccatag ttgcctgact ccccgtcgtg tagataacta cgatacggga    9540
gggcttacca tctggcccca gtgctgcaat gataccgcga acccacgct caccggctcc    9600 agatttatca gcaataaacc agccagccgg aaggggccgag cgcagaagtg gtcctgcaac    9660
tttatccgcc tccatccagt ctattaattg ttgccgggaa gctagagtaa gtagttcgcc    9720
agttaatagt ttgcgcaacg ttgttgccat tgctgcaggc atcgtggtgt cacgctcgtc    9780
gtttggtatg gcttcattca gctccggttc ccaacgatca aggcgagtta catgatcccc    9840
catgttgtgc aaaaaagcgg ttagctcctt cggtcctccg atcgttgtca gaagtaagtt    9900
ggccgcagtg ttatcactca tggttatggc agcactgcat aattctctta ctgtcatgcc    9960
atccgtaaga tgcttttctg tgactggtga gtactcaacc aagtcattct gagaatagtg    10020
tatgcggcga ccgagttgct cttgcccggc gtcaacacgg gataataccg cgccacatag    10080
```

```
cagaacttta aaagtgctca tcattggaaa acgttcttcg gggcgaaaac tctcaaggat    10140
cttaccgctg ttgagatcca gttcgatgta acccactcgt gcacccaact gatcttcagc    10200
atcttttact ttcaccagcg tttctgggtg agcaaaaaca ggaaggcaaa atgccgcaaa    10260
aaagggaata agggcgacac ggaaatgttg aatactcata ctcttccttt ttcaatatta    10320
ttgaagcatt tatcagggtt attgtctcat gagcggatac atatttgaat gtatttagaa    10380
aaataaacaa ataggggttc cgcgcacatt tccccgaaaa gtgccacctg acgtctaaga    10440
aaccattatt atcatgacat taacctataa aaataggcgt atcacgaggc cctttcgtct    10500
tcaa                                                                 10504

<210> SEQ ID NO 14
<211> LENGTH: 29
<212> TYPE: DNA
<213> ORGANISM: Artificial sequence
<220> FEATURE:
<223> OTHER INFORMATION: Synthesized: Primer mdy27

<400> SEQUENCE: 14
tcggaagatc tcatggtcaa cgagttcgc                                       29

<210> SEQ ID NO 15
<211> LENGTH: 32
<212> TYPE: DNA
<213> ORGANISM: Artificial sequence
<220> FEATURE:
<223> OTHER INFORMATION: Synthesized: Primer mdy39

<400> SEQUENCE: 15
tagtactaag cttcttgagc tcttccttct gc                                   32
```